United States Patent
Kunio et al.

(10) Patent No.: US 11,571,129 B2
(45) Date of Patent: Feb. 7, 2023

(54) DETECTING AND DISPLAYING STENT EXPANSION

(71) Applicant: CANON U.S.A., INC., Melville, NY (US)

(72) Inventors: Mie Kunio, Boston, MA (US); Daisuke Yamada, Cambridge, MA (US); Yohei Minatoya, Syosset, NY (US)

(73) Assignee: Canon U.S.A., Inc., Melville, NY (US)

( * ) Notice: Subject to any disclaimer, the term of this patent is extended or adjusted under 35 U.S.C. 154(b) by 1127 days.

(21) Appl. No.: 16/148,421

(22) Filed: Oct. 1, 2018

(65) Prior Publication Data

US 2019/0099080 A1  Apr. 4, 2019

Related U.S. Application Data

(63) Continuation-in-part of application No. 15/723,633, filed on Oct. 3, 2017, now Pat. No. 10,621,748.

(51) Int. Cl.
*A61B 5/00* (2006.01)
*A61F 2/92* (2013.01)
(Continued)

(52) U.S. Cl.
CPC .......... *A61B 5/0066* (2013.01); *A61B 5/0084* (2013.01); *A61B 5/6852* (2013.01);
(Continued)

(58) Field of Classification Search
CPC ............................ A61B 5/0066; A61B 5/0084
See application file for complete search history.

(56) References Cited

U.S. PATENT DOCUMENTS 5,357,550 A   10/1994  Asahina et al.
6,565,514 B2   5/2003  Svanerudh et al.
(Continued)

FOREIGN PATENT DOCUMENTS

JP   2012-505669 A   3/2012
JP   2017-527418 A   9/2017

OTHER PUBLICATIONS

Prati, et al., "Clinical Impact of OCT Findings During PCI: The CLI-OPCI II Study," JACC Cardiovasc Imaging, vol. 8, No. 11, 2015, pp. 1297-1305.
(Continued)

*Primary Examiner* — Joseph M Santos Rodriguez
(74) *Attorney, Agent, or Firm* — Canon U.S.A., Inc. I.P. Division

(57) ABSTRACT

A method for processing an intravascular image including a plurality of image frames acquired during a pullback of an imaging catheter inserted into a vessel, the method including displaying on a graphical user interface (GUI) an image including detected results of lumen borders and at least one stent, the image including an evaluated stent expansion and an evaluated stent apposition determined from the intravascular image. The method also includes determining whether a modification to the detected results of the stent has been received by the GUI. Then, re-evaluating stent length, stent expansion and stent apposition when it is determined that the detected results of the stent has been modified via the GUI and displaying the re-evaluated stent expansion and the re-evaluated stent apposition on the GUI.

20 Claims, 26 Drawing Sheets

(51) Int. Cl.

| | | |
|---|---|---|
| A61B 8/12 | (2006.01) | |
| G06F 3/048 | (2013.01) | |
| G06F 3/0488 | (2022.01) | |
| G16H 30/40 | (2018.01) | |
| G06T 7/00 | (2017.01) | |
| G16H 10/60 | (2018.01) | |
| G16H 30/20 | (2018.01) | |
| A61B 5/06 | (2006.01) | |
| A61B 5/107 | (2006.01) | |

(52) U.S. Cl.
CPC .............. *A61B 5/7435* (2013.01); *A61B 8/12* (2013.01); *A61F 2/92* (2013.01); *G06F 3/048* (2013.01); *G06F 3/0488* (2013.01); *G16H 30/40* (2018.01); *A61B 5/0035* (2013.01); *A61B 5/06* (2013.01); *A61B 5/1076* (2013.01); *G06T 7/0012* (2013.01); *G06T 2207/10101* (2013.01); *G16H 10/60* (2018.01); *G16H 30/20* (2018.01)

(56) References Cited

U.S. PATENT DOCUMENTS

| | | | |
|---|---|---|---|
| 6,763,261 | B2 | 7/2004 | Casscells et al. |
| 7,366,376 | B2 | 4/2008 | Shishkov et al. |
| 7,414,779 | B2 | 8/2008 | Huber et al. |
| 7,843,572 | B2 | 11/2010 | Tearney et al. |
| 7,916,387 | B2 | 3/2011 | Schmitt |
| 7,978,916 | B2 | 7/2011 | Klingensmith et al. |
| 8,175,684 | B2 | 5/2012 | Vaillant et al. |
| 8,315,282 | B2 | 11/2012 | Huber et al. |
| 8,325,419 | B2 | 12/2012 | Schmitt |
| 8,412,312 | B2 | 4/2013 | Judell et al. |
| 8,478,387 | B2 | 7/2013 | Xu |
| 8,493,567 | B2 | 7/2013 | Inoue |
| 8,565,859 | B2 | 10/2013 | Wang et al. |
| 8,581,643 | B1 | 11/2013 | Schmitt |
| 8,909,323 | B2 | 12/2014 | Baumgart |
| RE45,534 | E | 6/2015 | Huennekens et al. |
| 9,087,368 | B2 | 7/2015 | Tearney et al. |
| 9,121,926 | B2 | 9/2015 | Nair et al. |
| 9,138,147 | B2 | 9/2015 | Schmitt et al. |
| 9,173,591 | B2 | 11/2015 | Elbasiony et al. |
| 9,207,064 | B2 | 12/2015 | Inoue |
| 9,286,673 | B2 | 3/2016 | Begin et al. |
| 9,292,918 | B2 | 3/2016 | Zagrodsky et al. |
| 9,295,450 | B2 | 3/2016 | Furuichi et al. |
| 9,301,687 | B2 | 4/2016 | Kemp |
| 9,307,926 | B2 | 4/2016 | Begin et al. |
| 9,351,698 | B2 | 5/2016 | Dascal et al. |
| 9,462,950 | B2 | 10/2016 | Xu |
| 9,833,221 | B2 | 12/2017 | Hutchins et al. |
| 2010/0094127 | A1 | 4/2010 | Xu |
| 2011/0245650 | A1 | 10/2011 | Kerwin et al. |
| 2014/0276011 | A1 | 9/2014 | Schmitt et al. |
| 2015/0250438 | A1 | 9/2015 | Bozkaya et al. |
| 2015/0272442 | A1 | 10/2015 | Motafakker-Fard et al. |
| 2016/0022208 | A1 | 1/2016 | Gopinath |
| 2016/0171711 | A1 | 6/2016 | Gopinath et al. |
| 2016/0335766 | A1* | 11/2016 | Ambwani .............. A61B 34/20 |
| 2017/0020392 | A1 | 1/2017 | Xu |
| 2017/0024532 | A1 | 1/2017 | Gopinath et al. |

OTHER PUBLICATIONS

Horsley, E., "Imaging for the Future; Intravascular Optical Coherence Tomography", Sep. 10, 2016, from https://www.slideshare.net/ErnestHorsley/coronary-optical-coherence-tomography-oct-angio-coregistration-acr-and-metal-stent-optimisation-mso-softwarefrom.

St Jude Web Page "OPTIS Stent Optimization Software", downloaded Oct. 2, 2017, https://www.sjmglobal.com/professionals/resources-and-reimbursement/technical-resources/vascular/intravascular-diagnostics-and-imaging/intravascular-diagnostics-and-imaging-system-ffr-oct/optis-metallic-stent-optimization-software?halert=show&clset=92f57278-460e-4300-b7fe-89e52a04194f%3acadddb93-fcc4-47f2-8ceb-fd88f01ca17f.

Maehara, et al., "Assessment and Quantification of Stent Results by Intracoronary Optical Coherence Tomography," Intervent Cardiol Clin, Jul. 2015, vol. 4, Issue 3, pp. 285-294.

Bernelli, et al., "Percutaneous Coronary Intervention Planning and Optimization with Optical Coherence Tomography," Intervent Cardiol Clin, Jul. 2015, vol. 4, Issue 3, pp. 251-284.

Hebsgaard, L., et al, "Co-registration of optical coherence tomogrpahy and X-ray angiography in percutaneous coronary intervention. The Does Optical Coherence Tomography Optimize Revascularization (DOCTOR) fusion study", Internation Journal of Cardiology, 2015, pp. 272-278, vol. 182.

Kraus, M.F., et al., "Motion correction in optical coherence tomography volumes on a per A-scan basis using orthogonal scan patterns", Bio Med Express, Jun. 1, 2012, pp. 1182-1199, vol. 3, No. 6.

Reiber, J., et al, "QCA, IVUS and OCT in interventional cardiology in 2011", Cardiovascular Diagnosis and Therapy, Submitted Sep. 16, 2011, Accepted for publication Sep. 24, 2011, pp. 57-70, vol. 1, No. 1.

Bourantas, C. V., et al, "A new methodology for accurate 3-dimensional coronary artery reconstruction using routine intravascular ultrasound and angiographic data: implications for widespread assessment of endothelial shear stress in humans", Euro Intervention, Apr. 2013, pp. 582-593, vol. 9.

Bourantas, C. V., et al, "Bioresorbable vascular scaffold treatment induces the formation of neointimal cap that seals the underlying plaque without compromising the luminal dimensions: a concept based on serial optical coherence tomography data", Euro Intervention, Oct. 2014.

Tu, S., et al, "In vivo flow simulation at coronary bifurcation reconstructed by fusion of 3-Dimensional X-ray angiography and optical coherence tomography", Circ Cardiovasc Interv, Apr. 2013, pp. e15-e17.

Daisuke Nakamura, MD, et al., "New Volumetric Analysis Method for Stent Expansion and its Correlation With Final Fractional Flow Reserve and Clinical Outcome", JACC: Cardiovascular Interventions, vol. 11, No. 15, Aug. 13, 2018, pp. 1467-1478.

Photograph of a Slide of OCT Pullback, obtained at TCT Conference on Sep. 27, 2019, Slide presented at TCT Conference—Sep. 26-27, 2019 (1 page).

Hiram Grando Bezerra, MD, PhD, "How Do You React to the Automatic Expansion Data with OCT? A Case-Based Review of Using Volumetric Expansion Data", Cardiovascular Research Foundation, 2019 TCT conference, Sep. 28, 2019 (49 pages) (https://www.tctmd.com/slide/how-do-you-react-automatic-expansion-data-oct-case-based-review-using-volumetric-expansion).

Prati, et al., "Clinical Impact of OCT Findings During PCI: The CLI-OPCI II Study," JACC Cardiovasc Imaging, vol. 8, No. 11, Nov. 2015, pp. 1297-1305.

Hebsgaard, L., et al., "Co-registration of optical coherence tomography and X-ray angiography in percutaneous coronary intervention. The Does Optical Coherence Tomography Optimize Revascularization (DOCTOR) fusion study", International Journal of Cardiology, Mar. 2015, pp. 272-278, vol. 182.

\* cited by examiner

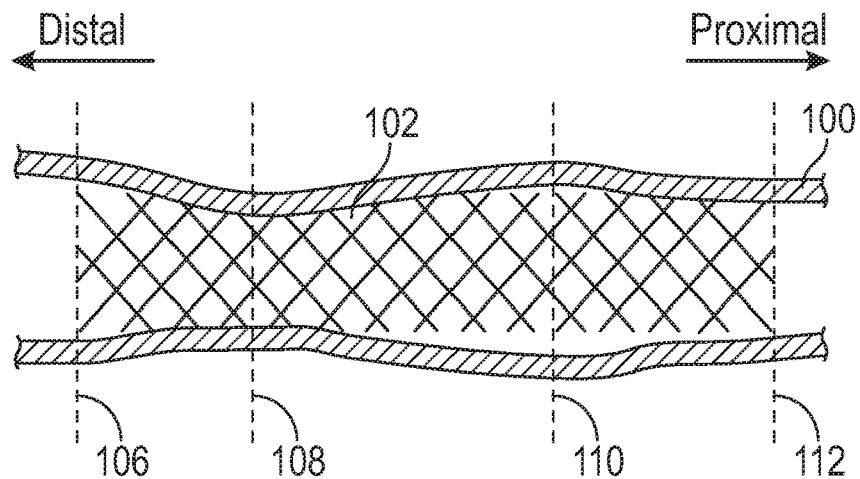
FIG. 4A
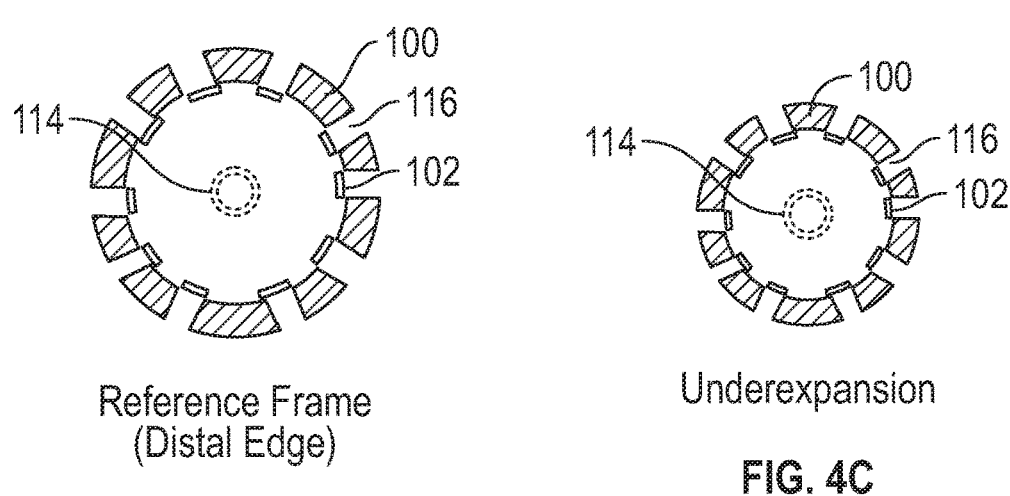
Reference Frame
(Distal Edge)
FIG. 4B
Underexpansion
FIG. 4C
Malapposition
FIG. 4D
Reference Frame
(Proximal Edge)
FIG. 4E

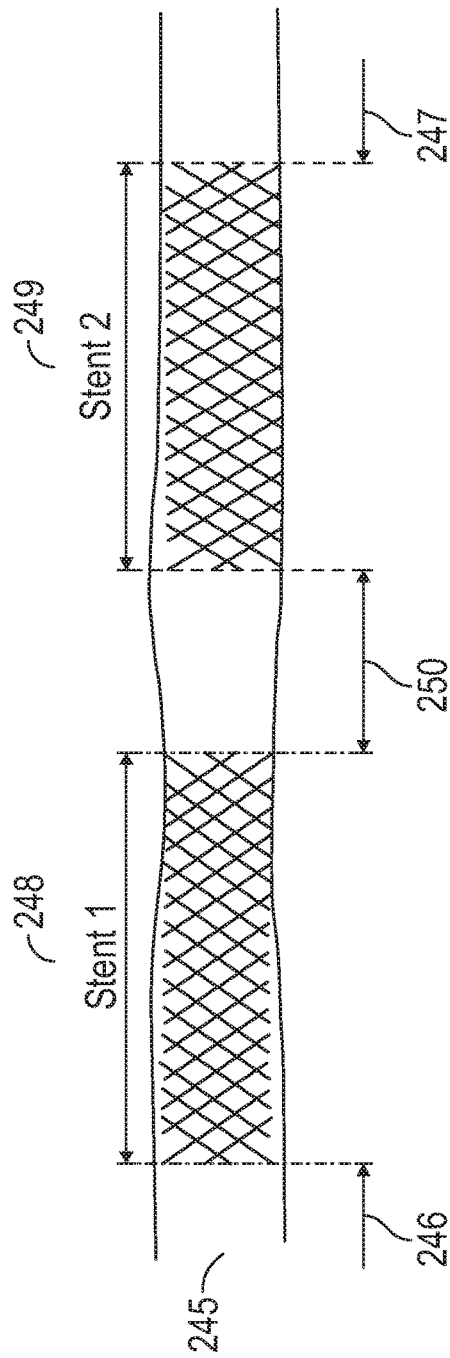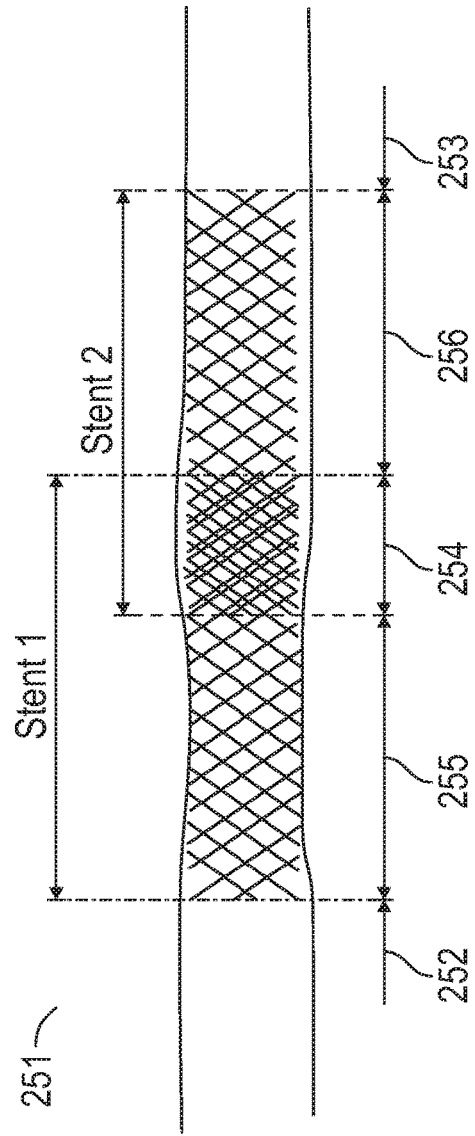
FIG. 23
FIG. 24

Actual Situation

Detected Result A

Detected Result B

DETECTING AND DISPLAYING STENT EXPANSION

CROSS-REFERENCE TO RELATED APPLICATIONS

This application is a Continuation in part of, and claims the benefit, of U.S. patent application Ser. No. 15/723,633, presently pending and filed on Oct. 3, 2017, which application is hereby incorporated by reference herein in its entirety.

BACKGROUND

Field of the Disclosure

The present disclosure relates in general to detecting stent expansion of a stent implanted in the vessel of a patient, and more particularly, to interpret information with an ability to re-evaluate the interpreted information after a user modification using a graphical user interface (GUI) to optimize stenting based on an acquired intravascular image.

Description of the Related Art

Intravascular imaging is a catheter-based imaging which captures images perpendicular to an imaging catheter. The imaging catheter is inserted and delivered to a target vessel region to obtain a cross-sectional view of the vessel. Intravascular images enable evaluating a lumen and an implanted device simultaneously. Therefore, intravascular imaging is suitable in navigating physicians to optimize percutaneous coronary intervention (PCI) procedures. One type of PCI procedure includes a stenting procedure involving implanting a stent in a patient's blood vessel such as a coronary artery. A few types of intravascular imaging modalities include intravascular ultrasound (IVUS), optical coherence tomography (OCT) and multi-modality OCT (MM-OCT).

There are many possible adverse outcomes after a PCI procedure. Clinical studies have shown that adverse outcomes associated with stenting were correlated to stent underexpansion where the stent is not sufficiently expanded within the vessel and stent malapposition where the implanted stent is not attached to the lumen. Even with intravascular imaging, which has an ability to detect stent underexpansion and/or stent malapposition, it is difficult for interventional cardiologists to avoid adverse outcomes associated with stenting because current GUIs may still not be optimal to interpret the information and optimize stenting based on the information acquired during the PCI procedure. One type of GUI associated with an OCT system is able to identify the minimal lumen area, but this can be considered as an indicator of stent underexpansion only when the measurement of minimum lumen area is located within the stented segment. When stent underexpansion exists at multiple locations, it may be problematic since the current GUI will not be able to identify every location where stent underexpansion exists.

Clinical studies that use IVUS have demonstrated that minimum stent area after a PCI procedure could be a strong procedural predictor of stent thrombosis and restenosis. Studies with OCT have also demonstrated that minimum stent area could predict future adverse events. Based on these studies, it is proposed to use stent expansion value to determine whether to intervene during stenting procedure. Stent expansion may be calculated by obtaining a stent area and dividing the stent area by an average reference lumen area. The result is then multiplied by 100 to obtain a stent expansion value in percent form. The reference lumen area may be determined from selecting a slice of the vessel having the largest lumen area within a reference segment. For example, if the stent expansion value is only 70% or less, the cardiologist may decide to intervene.

Determining the reference lumen area by selecting a slice of the vessel having the largest lumen area within a reference segment may not provide optimal results. Thus, another issue includes how to determine reference frames and the region to evaluate. The current criterion for selecting reference frames requires visual assessment by an interventional cardiologist (i.e., a user), which may not be ideal for the analysis during the PCI procedure.

Thus, there is a need in the art for determining appropriate reference frames to evaluate stent expansion within a confirmed stented segment. There is also a need to confirm the quality of OCT pullback for image processing, and to display the evaluated stent expansion and stent malapposition in a longitudinal direction in the stented segment and an indicator for indicating a level of stent expansion and stent malapposition along the longitudinal direction in the stented segment, as well as a need for re-evaluating stent expansion and stent malapposition after a user modification using a GUI.

SUMMARY

The present disclosure is directed to processing an intravascular image such as an OCT image including a plurality of image frames acquired during a pullback of an imaging catheter inserted into a vessel to provide a user with information regarding a stent implanted in the vessel during percutaneous coronary intervention (PCI). The user may refer to a display to view the stent implanted in the vessel of a patient during PCI along with indicators on a GUI representing a level of stent expansion, a level of stent apposition, or a percentage difference between an actual stent length and a calculated stent length. The user may refer to the indicator for the level of stent expansion to determine whether stent underexpansion has occurred at multiple locations throughout an entire range of the stent that is implanted. Similarly, the user may refer to the indicator for the level of stent apposition to determine whether the stent is well-apposed or malapposed at different locations throughout the entire range of the stent that is implanted. The user may also refer to the percentage difference between the actual stent length and a calculated stent length to confirm whether the quality of the pullback is sufficient, for example, for any image processing. If the user modifies the detected result(s) of a stent and/or a lumen border using the GUI, the stent expansion and stent apposition may be re-evaluated based on the user modification.

One embodiment of the present disclosure is directed to a method for processing an intravascular image including a plurality of image frames acquired during a pullback of an imaging catheter inserted into a vessel. The method includes displaying on a GUI an image including detected results of lumen borders and at least one stent, the image including an evaluated stent expansion and an evaluated stent apposition determined from the intravascular image. The method also includes determining whether a modification to the detected results of the stent has been received by the GUI. Then, re-evaluating stent length, stent expansion and stent apposition when it is determined that the detected results of the stent has been modified via the GUI and displaying the re-evaluated stent expansion and the re-evaluated stent apposition on the GUI.

Further features of the present disclosure will become apparent from the following description of exemplary embodiments with reference to the attached drawings.

BRIEF DESCRIPTION OF THE DRAWINGS

FIG. 4A is a schematic diagram illustrating a lumen and a stent in a longitudinal direction in accordance with one or more aspects of the present disclosure;

FIGS. 4B-4E are schematic diagrams illustrating OCT image frames displaying the lumen and the stent displayed in FIG. 4A along various positions of a range in a stented segment in accordance with one or more aspects of the present disclosure;

FIG. 23 is a diagram illustrating implantation of two stents with no overlap;

FIG. 24 is a diagram illustrating implantation of two stents with partial overlap;

DETAILED DESCRIPTION

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

The present disclosure includes image processing of an intravascular image including a plurality of image frames acquired during a pullback of an imaging catheter inserted into a vessel to provide a user with information regarding a stent implanted in the vessel during percutaneous coronary intervention (PCI). The user may refer to a display to view the stent implanted in the vessel of a patient during PCI along with indicators representing a level of stent expansion, a level of stent apposition, or a percentage difference between an actual stent length and a calculated stent length. The user may refer to the indicator for the level of stent expansion to determine whether stent underexpansion has occurred at multiple locations throughout an entire range of the stent that is implanted. The user may also refer to an indicator for the level of stent apposition to determine whether the stent is well-apposed or malapposed at different locations throughout the range of the stent that is implanted.

The user may also refer to the percentage difference between the actual stent length and a calculated stent length to confirm whether the quality of the pullback is sufficient, for example, for any image processing.

Intravascular imaging modality is a catheter-based imaging, of which images are captured perpendicular to an imaging catheter. The imaging catheter is inserted and delivered to a target vessel region. The intravascular imaging modality allows for visualizing the vessel from a cross-sectional perspective, which enables the evaluation of a lumen and an implanted device simultaneously. Therefore, this type of imaging modality is suitable to navigate physicians to optimize PCI procedures, especially stenting procedures. The present disclosure describes a method to detect and display stent expansion information to improve stenting outcomes. Although image processing of an OCT image is described herein, any type of intravascular image including a plurality of image frames may be used interchangeably with an OCT image.

Figure 1:
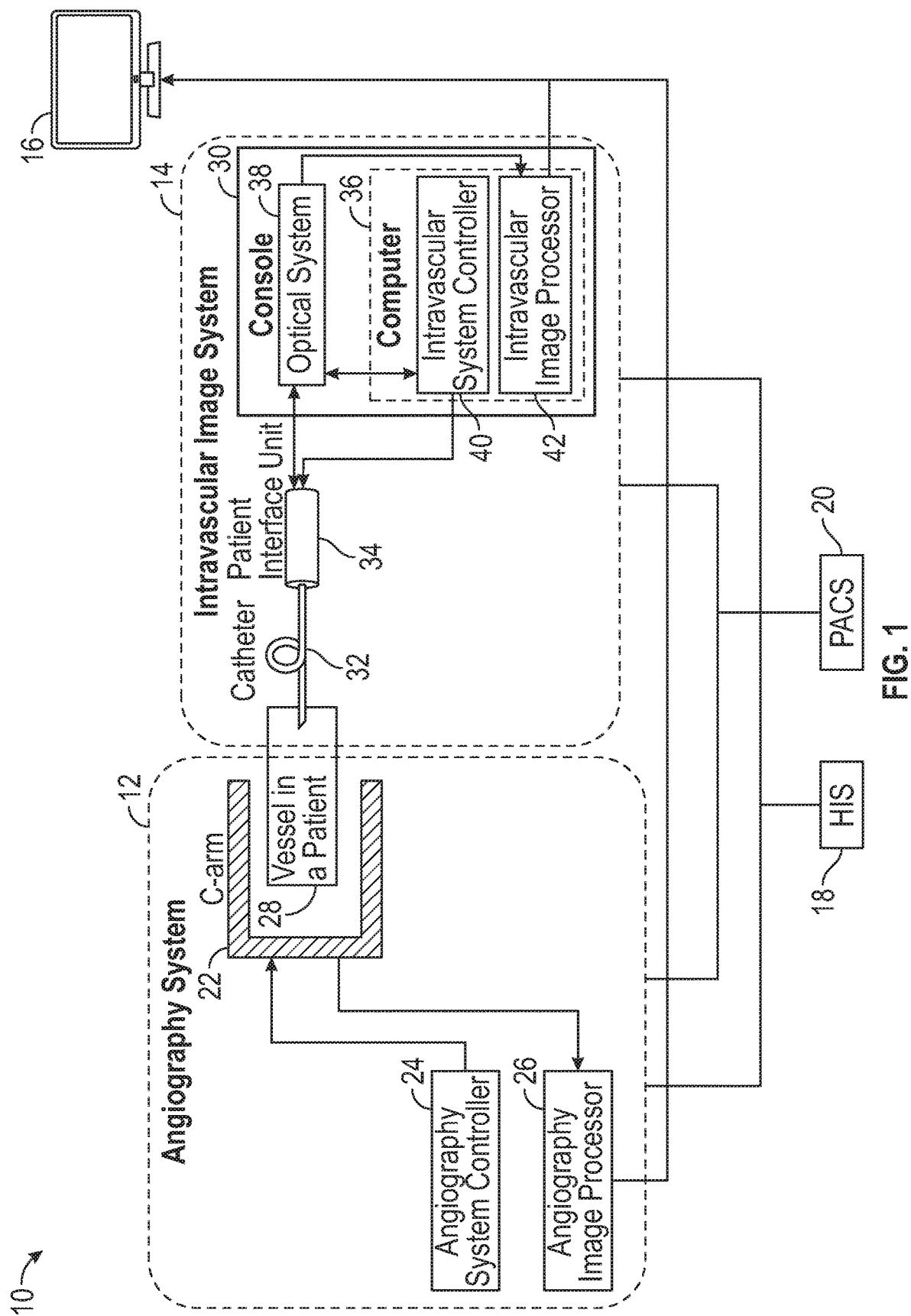
FIG. 1 is a schematic diagram illustrating imaging modalities for use during a PCI procedure to detect and display stent expansion in accordance with one or more aspects of the present disclosure.

FIG. 1 shows a schematic diagram of an exemplary imaging system 10 including various connections that may be used during a PCI procedure. The imaging system 10 includes an angiography system 12, an intravascular image system 14, a display 16 and a system that stores patient data such as a Hospital Information System (HIS) 18 and/or a Picture Archiving and Communication System (PACS) 20. The angiography system 12 includes an X-ray imaging device such as a C-arm 22 that is connected to an angiography system controller 24 and an angiography image processor 26 for acquiring angiography images of a vessel in a patient 28.

The imaging system 10 also includes an intravascular imaging system 14 which consists of a console 30, a catheter 32 and a patient interface unit 34 that connects between the catheter 32 and the console 30 for acquiring intravascular images. The patient interface unit 34 includes a motor (not shown) to enable pullback of imaging optics during image acquisition. The console 30 includes a computer 36 and an optical system 38 that includes one or two light source(s). A processor of the computer 36 may function as a system controller 40 and an intravascular image processor 42. As the system controller 40, the processor controls the motor in the patient interface unit 34 and the optical system 38 to acquire an imaging signal. The image processor 42 receives the imaging signal from the optical system 38, performs steps for image processing and controls information to be displayed on a display 16. The intravascular image system 14 can be an intravascular ultrasound (IVUS) system, optical coherence tomography (OCT) system or multi-modality OCT (MM-OCT) system. In the present disclosure, OCT or MM-OCT system is used, however, any intravascular imaging modality that can visualize both a lumen and an implanted device may be used instead of OCT or MM-OCT system.

Figure 2:
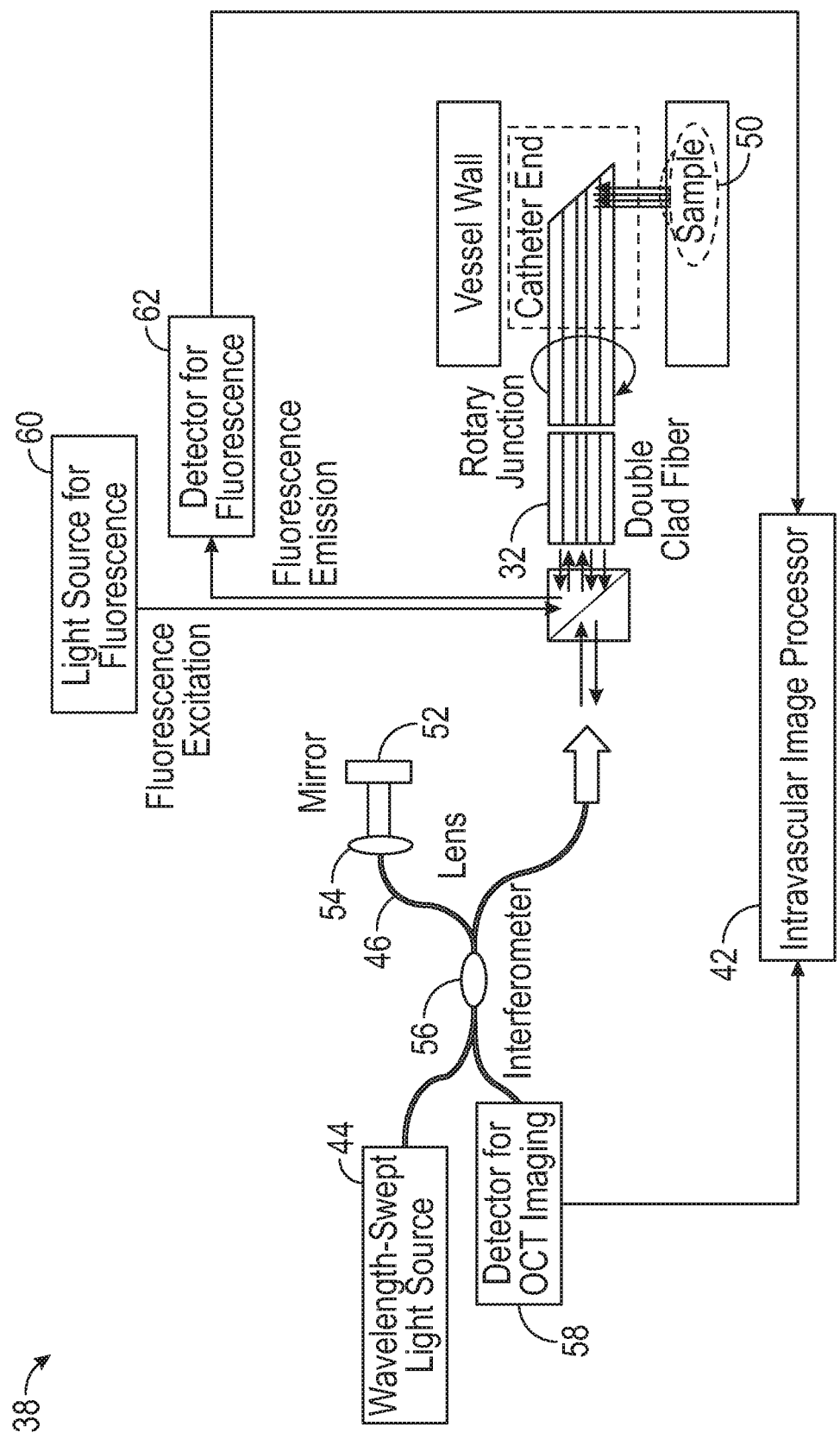
FIG. 2 is a schematic diagram illustrating an optical system of a multimodality optical coherence tomography (MM-OCT) system for acquiring an OCT image in accordance with one or more aspects of the present disclosure.

FIG. 2 is a schematic diagram illustrating details of the optical system 38 of the intravascular image system 14 (MM-OCT) with its connection to a catheter 32 and the image processor 42. In FIG. 2, the optical system 38 for swept-source OCT is described. The input light 44 from wavelength-swept light source is split into reference light 46 and sample light 48. The sample light 48 is irradiated to a sample 50, i.e., a vessel in a patient 28, through an optical fiber in the catheter 32 and its reflection (sample signal) is returned through the fiber in the catheter 32. The reference light 46 is reflected back by a mirror 52 and a lens 54 collects the reflection (reference signal). The sample signal and the reference signal are interfered at an interferometer 56 and the interfered signal is detected by a detector 58. The intravascular image processor 42 processes the detected signal and generates an OCT image. At the same time, for an MM-OCT system, another light 60 is irradiated to the sample in the same manner as the sample light. Fluorescence that is emitted from the sample 50 is delivered through the fiber in the catheter 32 and detected by another detector 62. The intravascular image processor processes 42 the detected signal and creates the fluorescence image with the OCT image.

Figure 3:
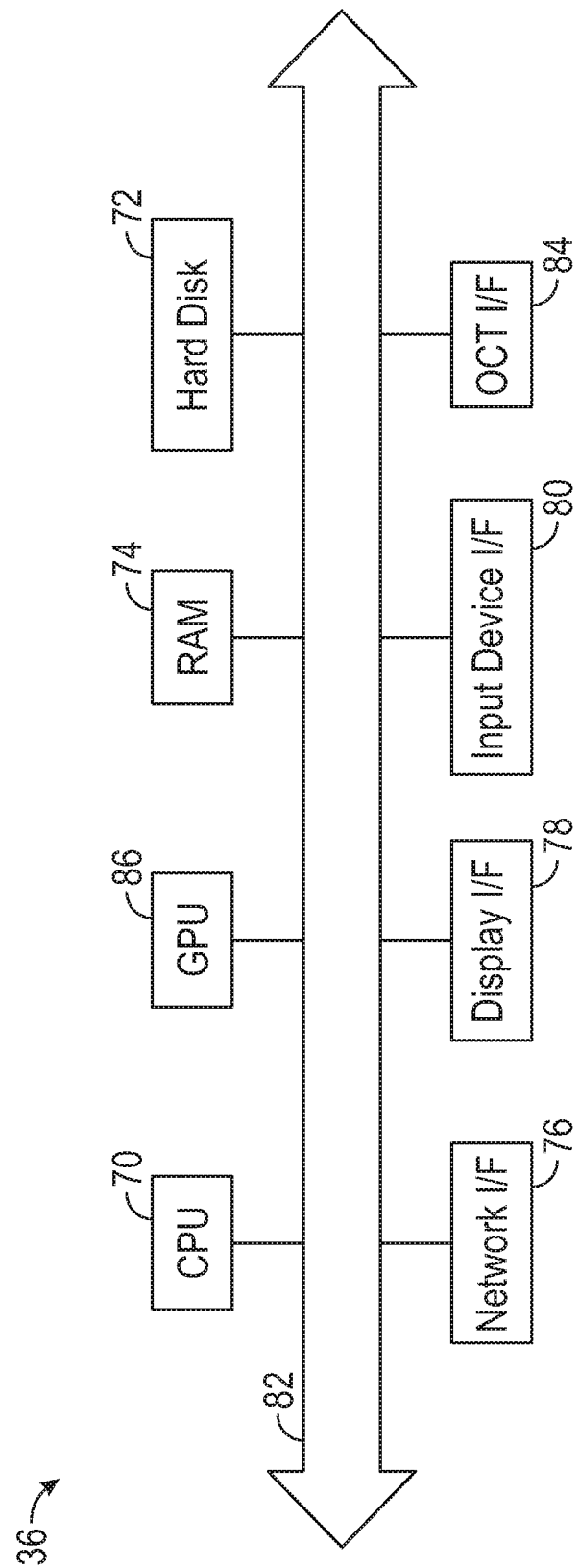
FIG. 3 is an exemplary block diagram illustrating a hardware configuration of a computer used in an OCT or MM-OCT system in accordance with one or more aspects of the present disclosure.

FIG. 3 is an exemplary block diagram of a hardware configuration of the computer 36 of the intravascular image system 14 (OCT or MM-OCT system). As described above, the processor of this computer 36 can work as the intravascular system controller 40 and the intravascular image processor 42. The central processing unit (CPU) 70 is configured to read computer-executable instructions stored in a storage medium, such as a hard disk 72, open on RAM 74, and perform the instructions in order. The computer-executable instructions include the calculation and/or methods that are described in the present disclosure, but they are not limited to. The processor for image processing may also be implemented in the angiography system 12 instead of the intravascular imaging system 14. Alternatively, the image processing may be implemented externally from the angiography system 12 and the intravascular image system 14 such as a stand-alone device encompassing an image processor (not shown).

The computer 36 includes a central processing unit ("CPU") 70, a ROM, a RAM 74, a network communication interface 76, a hard disk (and/or other storage device) 72, a display interface 78, a keyboard (or input interface; may also include a mouse or other input device in addition to the keyboard) 80 and a BUS 82 or other connection lines between one or more of the aforementioned components as shown in FIG. 3. The computer 36 includes an OCT interface 84 as well as a graphics processing unit (GPU) 86. The computer 300 may include one or more combinations of the other aforementioned components. The computer 36 may include one or more additional processors in addition to CPU 70, and such processors, including the CPU 70, may be used for acquiring information from an intravascular image system 14 and an angiography system 12 to detect and display stent expansion information to improve stenting outcomes. The computer 36 may further include one or more processors connected via a network connection (e.g., via network I/F 76). The CPU 70 and any additional processor being used by the computer 36 may be located in the same telecom network or in different telecom networks.

FIG. 4A is an exemplary longitudinal view of a lumen 100 and stent-struts 102. The stent-struts 102 form the implanted stent within the lumen borders from the position 106 at a distal end of the vessel to the position 112 at a proximal end of the vessel. The position 106 represents a distal edge of the stent. The position 112 represents a proximal edge of the stent. The positions 108 and 110 represent two additional points between the distal edge of the stent 106 and the proximal edge of the stent 112. Although only four vertically dashed lines are shown in FIG. 4A, additional vertically dashed lines representing other positions may be included between the distal and proximal edges of the stent (106, 112). Each vertical dashed line may represent a position that corresponds to an OCT image frame within the OCT image.

FIGS. 4B-E are OCT image frames representing cross-sectional views of the different positions (106, 108, 110, 112) shown in FIG. 4A. In FIGS. 4B-E, the dotted double-circle 114 at the center represents an imaged OCT imaging catheter. The black solid lines represent stent-struts 102 and the gray outer circle represents the lumen 100. A majority of stents currently used are metal-based stents. The use of metal based stents may result in a shadow 116 that is created underneath each stent-strut 102, which is represented by the non-filled area in the gray outer circle. If the stent is not a metal-based stent, the shadow may not appear and no non-filled area would exist. Once OCT pullback is finished, multiple OCT image frames are acquired along the imaging catheter. From the acquired images, two values may be evaluated: stent apposition and stent expansion. Stent apposition is assessed by measuring the distance between the lumen edge and the stent-struts in each OCT image frame. If the distance is larger than the stent-strut width, i.e., the stent-struts are away from the lumen edge, the stent is considered to be malapposed. Stent expansion is evaluated by comparing the stent area at a certain image frame to the stent area at a reference frame. If the stent area at the image frame that is focused is equal or almost equal to that at the reference frame, the stent is considered to be expanded sufficiently. The image frame that is captured at the edge of the stent may be used as a reference frame.

FIG. 4B is an image frame illustrating a cross-sectional view of the lumen 100 and stent-struts 102 at the position 106 shown in FIG. 4A. The image frame at 106 is located at a distal edge of the stent and may be used as a reference frame. FIG. 4E is an image frame illustrating a cross-sectional view of the lumen 100 and stent-struts 102 at the position 112 shown in FIG. 4A. The image frame at 112 is located at a proximal edge of the stent and may be used as a reference frame.

When stent apposition and stent expansion are evaluated, the stenting status can be assigned for each image frame. Table 1 shows the categorization of the post-stenting status. The ideal stenting scenario is when the stent is well-apposed and well expanded. Stent underexpansion is a scenario where the stent is well-apposed, but not well-expanded. FIG. 4C is an image frame illustrating a cross-sectional view of the lumen 100 and stent-struts 102 at the position 108 shown in FIG. 4A. The image frame at position 108 is an example of stent underexpansion. The stent is well-apposed because the distance between the lumen edge 100 and the stent-struts 102 is less than a width of the stent-strut 102, however, the lumen does not appear to be sufficiently expanded.

Stent malapposition is a situation where the stent is well-expanded, but is malapposed. FIG. 4D is an image frame illustrating a cross-sectional view of the lumen 100 and stent-struts 102 at the position 110 shown in FIG. 4A. The image frame at position 110 is an example of stent malapposition. The stent is malapposed because the distance between the lumen edge 100 and the stent-struts 102 is larger than the stent strut width. The lumen 100 appears to be sufficiently expanded in the image frame. If the stent is malapposed and not well-expanded, the stent might be undersized or improperly expanded. Since the OCT image includes a plurality of OCT image frames in the longitudinal direction, it is useful to evaluate stent expansion and stent apposition at each image frame within the OCT image to better evaluate the post-stenting status for the entire region of the implanted stent within the lumen 100 from a distal edge of the stent 106 to a proximal edge of the stent 112.

TABLE 1

Categorization of Post-Stenting Status

|  |  | Stent apposition | |
|---|---|---|---|
|  |  | Well-apposed | Malapposed |
| Stent expansion | Sufficient expansion | Ideal situation | Stent malapposition |
|  | Insufficient expansion | Stent underexpansion | Stent undersizing or Improper expansion |

Figure 5:
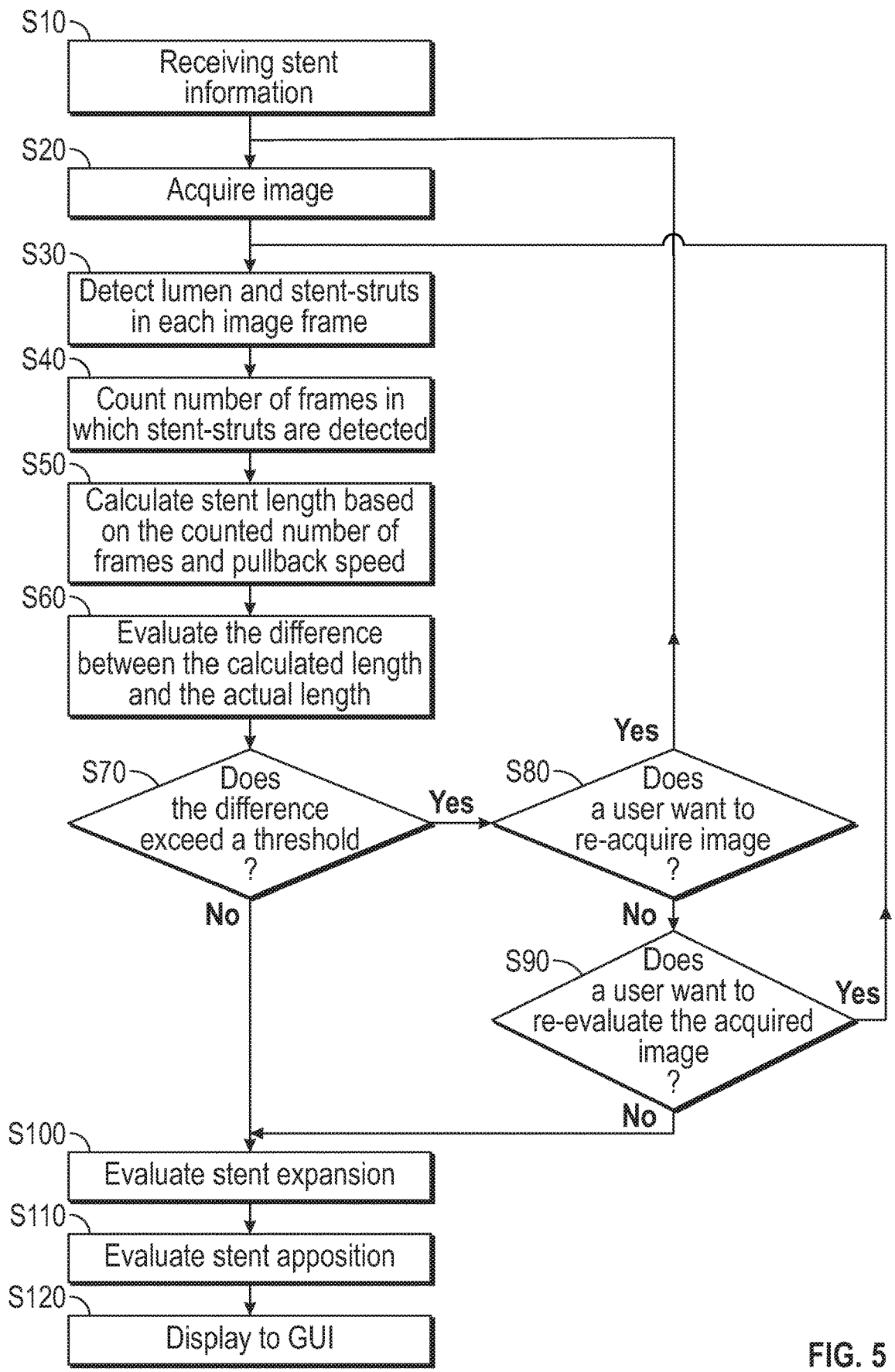
FIG. 5 is a flowchart illustrating a workflow for evaluating an OCT image including a plurality of OCT image frames in accordance with one or more aspects of the present disclosure.

FIG. 5 is a flowchart illustrating steps for evaluating an OCT image including a plurality of OCT image frames to detect and display stent expansion information to improve stenting outcomes. The first step of evaluating the OCT image is initiated with a processor receiving stent information in step S10. The stent information may include information such as stent length and stent-strut width by way of example and not of limitation. The processor could be an intravascular image processor, an angiography image processor or an external image processor. The information may be sent to the processor by direct input such as a nurse or technician with a touch panel, keyboard and/or audio command by way of example. The information may be sent to the processor by direct input from a product barcode that is scanned by the nurse or technician. The information may be sent to the processor by searching information in a database including patient care data such as HIS 18 and/or PACS 20. The stent length included in the information received in step S10 may be referred to as a first stent length.

Figure 6:
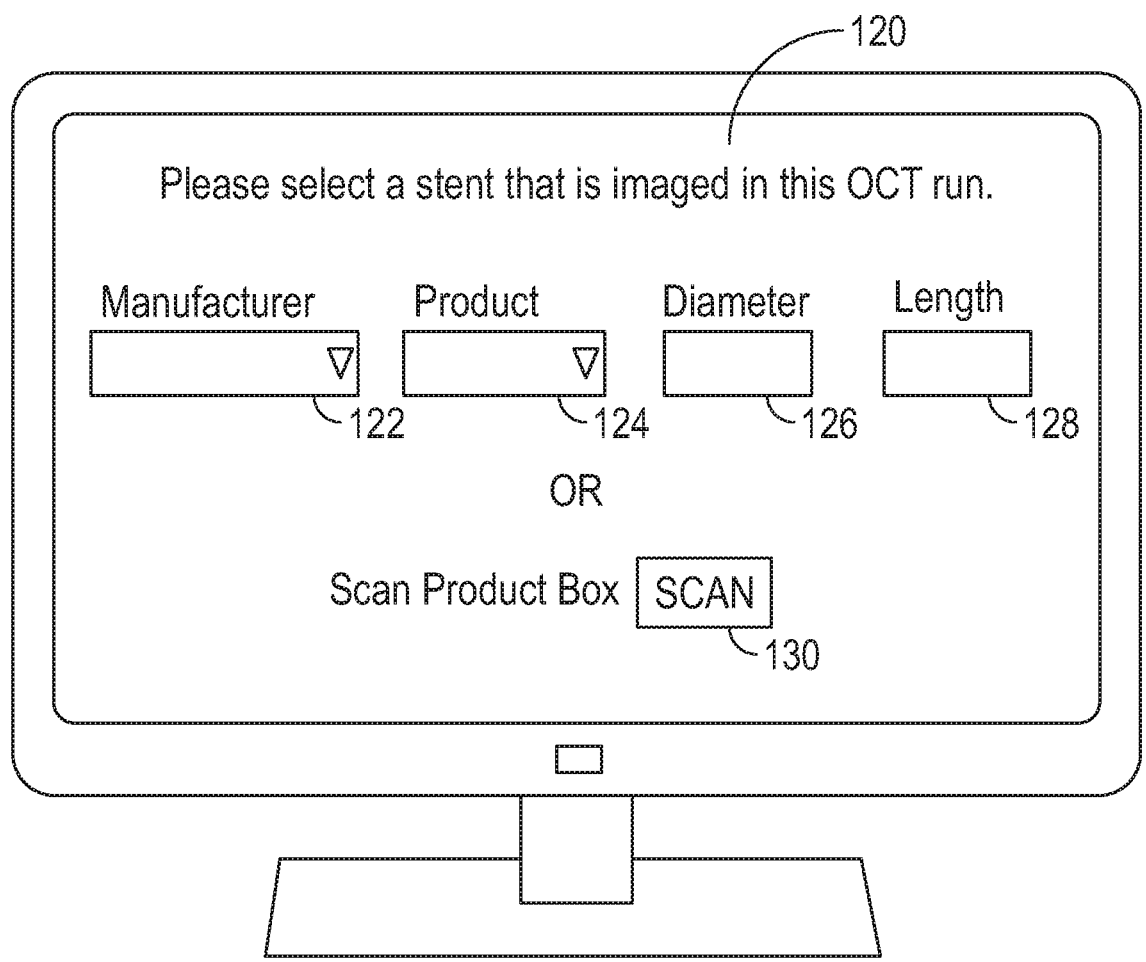
FIG. 6 illustrates an exemplary graphical user interface (GUI) screen for inputting stent information in accordance with one or more aspects of the present disclosure.

FIG. 6 is an exemplary graphical user interface (GUI) screen 120 that a nurse or a technician directly enters the stent information. In this example, a nurse or a technician can select a manufacturer 122 and product 124 and enter diameter 126 and length 128 of the stent. If the manufacturer 122 and/or product name are not available from the list or drop down menu, the nurse or technician may enter the information manually. Additionally, the nurse or technician may choose to scan 130 the barcode of the product, so that a processor can search the corresponding stent in a database. The stent information entered or retrieved by scanning is used to determine the actual stent length of a stent that is to be implanted in the vessel of a patient or a stent that has already been implanted in the vessel of the patient.

Referring back to FIG. 5, in step S20, an OCT image is acquired during OCT pullback. The OCT image includes a plurality of OCT image frames where each OCT image frame may correspond to a different position of the OCT pullback. Although step S20 is shown after the importing step S10 for importing stent information, the importing step S10 may occur any time after acquiring the OCT image but before comparing stent information to information obtained from the OCT image.

Steps S30, S40 and S50 involve calculating a stent length of a stent implanted in the vessel of a patient. The calculated stent length and the actual stent length obtained from stent information are derived differently. In step S30, the processor detects the lumen and stent-struts in each OCT image frame from the OCT image acquired in step S20. A stented segment of the OCT image includes all the OCT image frames within the OCT image in which stent-struts are detected. The stented segment therefore represents a portion of the vessel in which the stent is implanted. If any stent-struts are detected, the OCT image frame is categorized as a frame that is captured within the stented segment (Group $G_S$). Stent-struts can be detected with any available methods. For example, since stent-struts create a strong reflection at their surface and shadows underneath if a metal-based stent is used, the stent-struts can be detected by evaluating intensity change in the radial direction for each angle. After the detection, the quality of the detected stent-struts is checked for each OCT image frame captured within the stented segment. If multiple stents are implanted, each detected stent-strut needs to be categorized to the stent to which the detected stent-strut belongs. If CPU 70 already knows how many stents are implanted by, for example, having a user input the number of stents during the procedure, CPU 70 may perform this categorization by fitting the detected stent-struts into the circles and/or ovals whose number is already specified. If CPU 70 does not know the number of the implanted stents, CPU 70 may fit the detected stent-struts into the circles and/or ovals based on the distance from the center of the image and/or the distance between each detected stent-struts. In both cases, after fitting, CPU 70 may ask a user to check the fitting results. When multiple stents are implanted, the stented segment (Group $G_S$) should be created for each stent.

Table 2 below shows examples of criteria to remove the focused frame from the stented segment (Group $G_S$). Each criterion can be used alone or combined with other criteria.

TABLE 2

Example of criteria to remove the OCT image frame from the stented segment

| | |
|---|---|
| 1 | Only one stent-strut is detected |
| 2 | No stent-struts are detected in one quadrant |
| 3 | No stent-struts are detected in two consecutive quadrants |
| 4 | Maximum angle of two consecutive stent-struts exceeds the threshold angle. The threshold angle should be larger than 90° but smaller than 180° (e.g., 120°) |
| 5 | No stent-struts are detected in one quadrant of which axis is determined based on the guidewire location |
| 6 | No stent-struts are detected in two consecutive quadrants of which axis is determined based on the guidewire location |
| 7 | Both 2 and 5 are satisfied |
| 8 | Both 3 and 6 are satisfied |
| 9 | The oval that is fitted to the detected stent-struts is bigger than the detected lumen edge |

In step S40, a number of OCT image frames in which stent-struts are detected (Group $G_S$) is determined. Then in step S50, a stent length is calculated based on the number of OCT image frames and an OCT pullback speed. The stent length calculated in step S50 may also be referred to as a second stent length and the range along the vessel where the stent is detected is referred to as a stent region or stent range. In step S60, the calculated stent length is compared to the actual stent length obtained in step S10 from importing stent information to evaluate the difference between the calculated stent length and the actual stent length. In step S70, it is determined whether the difference between the calculated stent length and the actual stent length exceeds a predetermined threshold. In an ideal situation the calculated stent length equals the actual stent length. However, in practice the calculated stent length may not equal the actual stent length. The predetermined threshold may be preset to a certain value such as 10% by way of example. Alternatively, the predetermined threshold may be selected or modified by a user. When the difference between the calculated stent length and the actual stent length is 10%, it means that the calculated stent length is 10% shorter or longer than the actual stent length.

If it is determined in step S70 that the predetermined threshold has been exceeded (Yes in step S70), then the process proceeds to step S80 for determining whether a user wants to re-acquire the OCT image. If the user decides to re-acquire the OCT image (Yes in step S80), the process returns to step S20 for acquiring an OCT image. Alternatively, if the user decides not to re-acquire the OCT image (No in step S80), then the user decides whether to re-evaluate the acquired OCT image in step S90. If the user decides to re-evaluate the acquired OCT image (Yes in step S90), then the process returns to step S30 for detecting lumen and stent-struts in each OCT image frame. Alternatively, if the user decides not to re-evaluate the acquired OCT image (No in step S90), then the process proceeds to step S100 for evaluating stent expansion and stent apposition which is described in further detail with respect to FIGS. 9A, 9B, 14A and 14B.

Returning to step S70, if the difference between the calculated stent length and the actual stent length does not exceed the predetermined threshold (No in step S90), then the next step is to evaluate stent expansion in step S100. Subsequently, in step S110, stent apposition is evaluated. After evaluating stent expansion and apposition, the results are displayed in a GUI in step S120. The evaluation and display of stent apposition may be skipped based on a user's preference.

Figure 7:
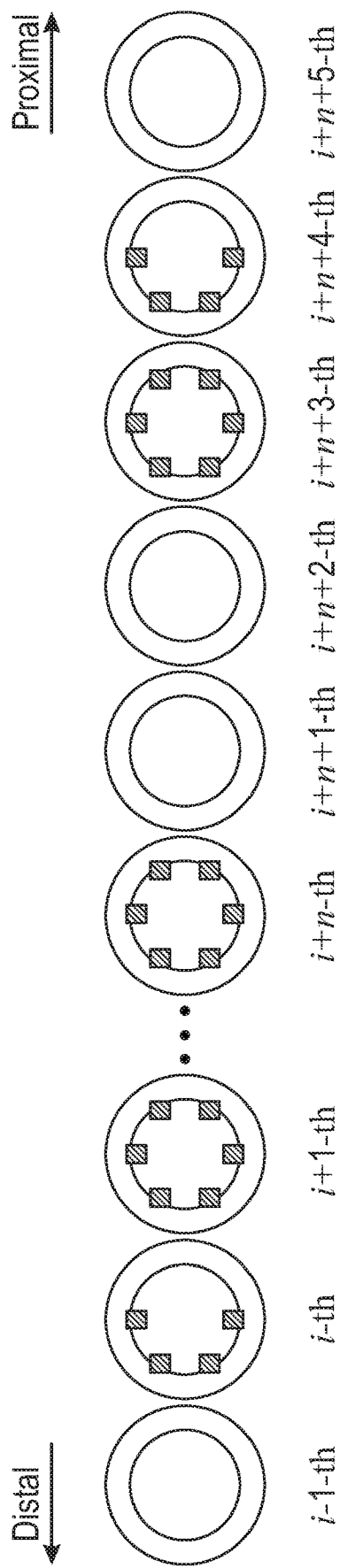
FIG. 7 is a schematic diagram illustrating a plurality of image frames in an OCT image from an OCT pullback affected by cardiac motion in accordance with one or more aspects of the present disclosure.

Due to cardiac motion, the OCT imaging catheter sometimes moves in the opposite direction to the pullback direction, and the region that is already captured by OCT may be recaptured during the same pullback. To avoid image processing errors when the OCT imaging catheter recaptures a same region during the pullback, if there is one or multiple frame(s) whose frame number is not continuous from one frame before or after in the stented segment (Group $G_S$) and if no stent-struts are detected in the OCT image frame(s) of the missing frame number (i+n+1–th and i+n+2–th frames in FIG. 7), the OCT image frames that are less continuous (i+n+3–th and i+n+4–th frames in FIG. 7) are excluded from counting as OCT image frames in which stent-struts are detected in the OCT image. In FIG. 7, when removing the less continuous frames, the calculated stent length is then based on all the OCT image frames between the i–th frame representing the distal edge and the i+n–th frame representing the proximal edge. Excluding the less continuous frames after the missing frame number may prevent incorrectly using a region that has already been captured during OCT pullback. Stent length is then calculated based on the counted number of frames and OCT pullback speed, and is compared with the actual stent length, which is obtained from the stent information. If the difference between the calculated and the actual stent lengths is greater than a predetermined threshold, a user such as a physician may determine whether to acquire another OCT image.

Figure 8:
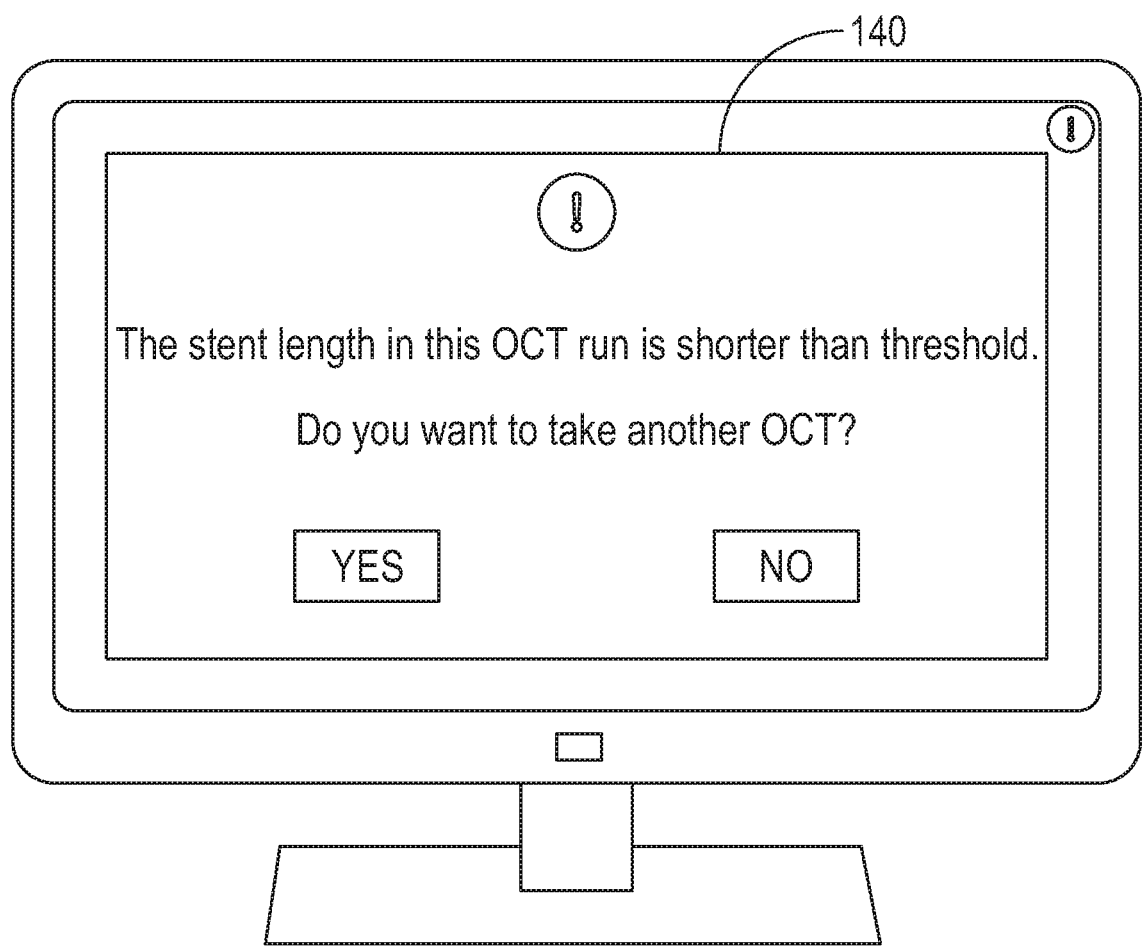
FIG. 8 illustrates an exemplary GUI screen for requesting a user to re-acquire an OCT image in accordance with one or more aspects of the present disclosure.

FIG. 8 is an exemplary GUI screen 140 that asks a user whether to re-acquire an OCT image. The GUI screen 140 may also show the difference between the calculated stent length and the actual stent length, so that a user may make an informed decision based on the difference in the calculated and actual stent lengths. If a user decides not to re-acquire an OCT image, a user can decide whether to re-evaluate the acquired OCT image. If a user decides to re-evaluate, the processor can repeat the same processes and/or a user can modify lumen and/or stent-struts detection. If two or more OCT images are acquired, and if the quality of the most recently acquired OCT image is not as good as the previously acquired OCT image, the user may select the previously acquired OCT image for further image processing. Subsequently, the processor evaluates stent expansion for each OCT image frame from the previously acquired OCT image that is within the stented segment (Group $G_S$), and displays the stent expansion level along the longitudinal view in the GUI.

Figure 9A:
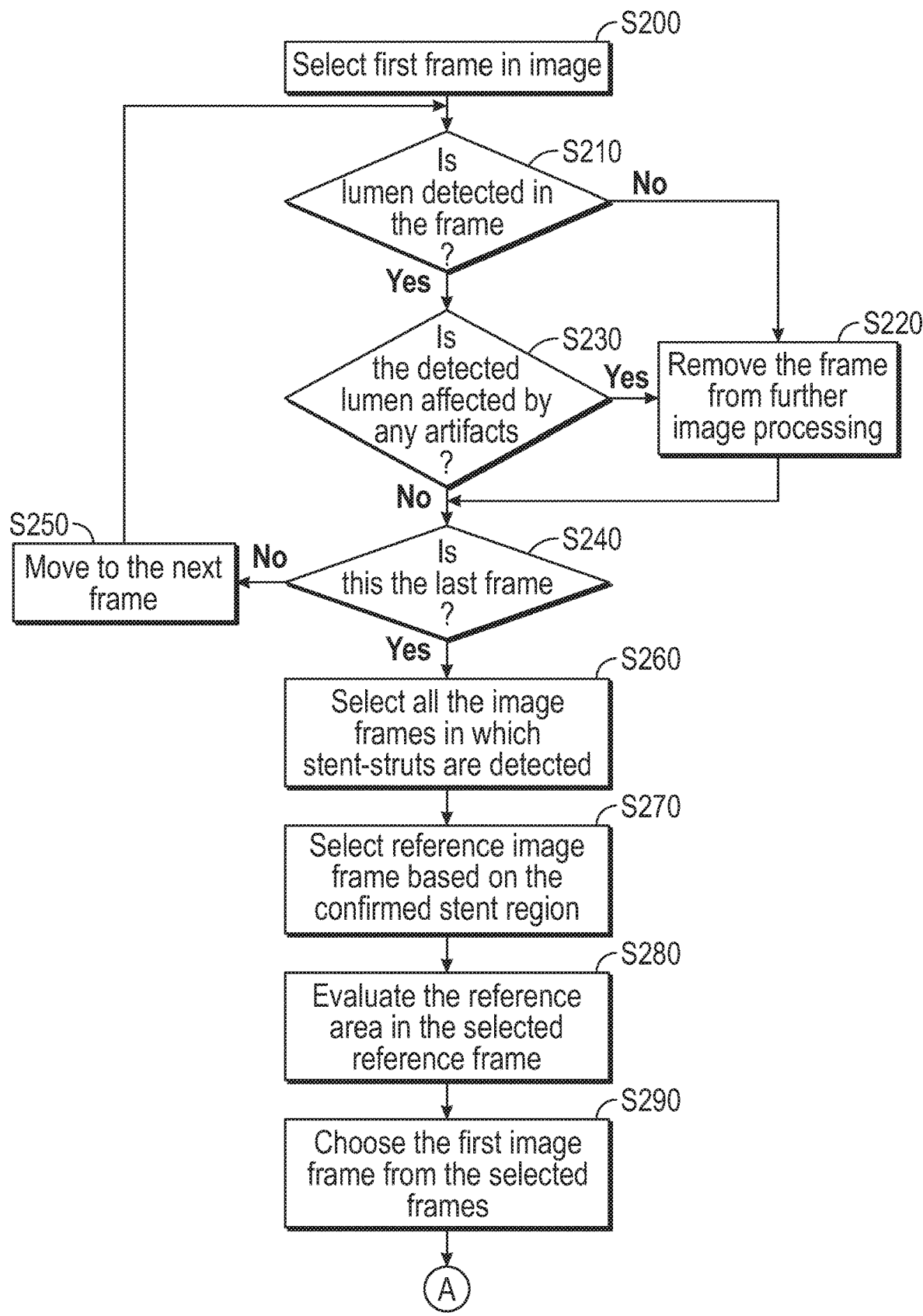
FIGS. 9A and 9B are flowcharts illustrating a workflow for evaluating stent expansion in accordance with one or more aspects of the present disclosure.

FIG. 9A is an exemplary flowchart illustrating various steps for evaluating stent expansion. Steps S200 through S250 function to remove inappropriate OCT image frames from the OCT image from further image processing. The result of lumen detection is checked for each OCT image frame. If the lumen is not detected or if the detected lumen is affected by any artifact, the OCT image frame is removed. A first OCT image frame is selected from the OCT image in a first step S200. After selecting the first OCT image frame in step S200, it is determined whether a lumen is detected in the selected OCT image frame in step S210. If it is determined in step S210 that no lumen has been detected in the OCT image frame (No in step S210), then the OCT image frame is removed from further image processing in step S220 and the process continues to step S240. Alternatively, if the lumen is detected in the frame (Yes in step S210), then a further determination of whether the detected lumen is affected by any artifact in step S230. If the detected lumen is affected by an artifact (Yes in step S230), then the OCT image frame is removed from further processing in step S220 and the process proceeds to step S240. If the detected lumen is not affected by any artifact (No in step S230), then it is determined in step S240 if the selected OCT image frame is the last OCT image frame from the OCT image. If the selected frame is not the last frame in the OCT image (No in step S240), then the next OCT image frame from the OCT image is selected in step S250 and the process returns to step S210. If the selected OCT image frame is the last OCT image frame (Yes in step S240), then the process proceeds to step S260.

Figure 10A:
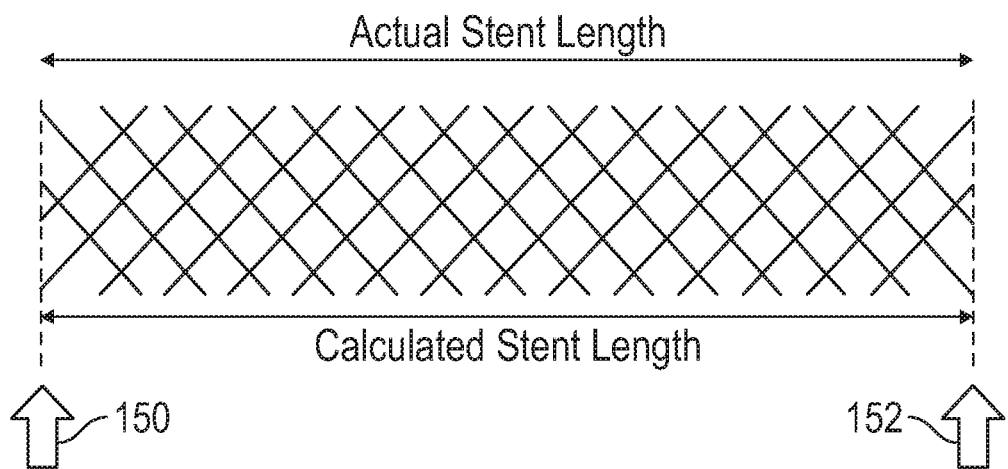
FIGS. 10A and 10B are diagrams illustrating examples for selecting reference frames for stent expansion evaluation in accordance with one or more aspects of the present disclosure.
Figure 10B:
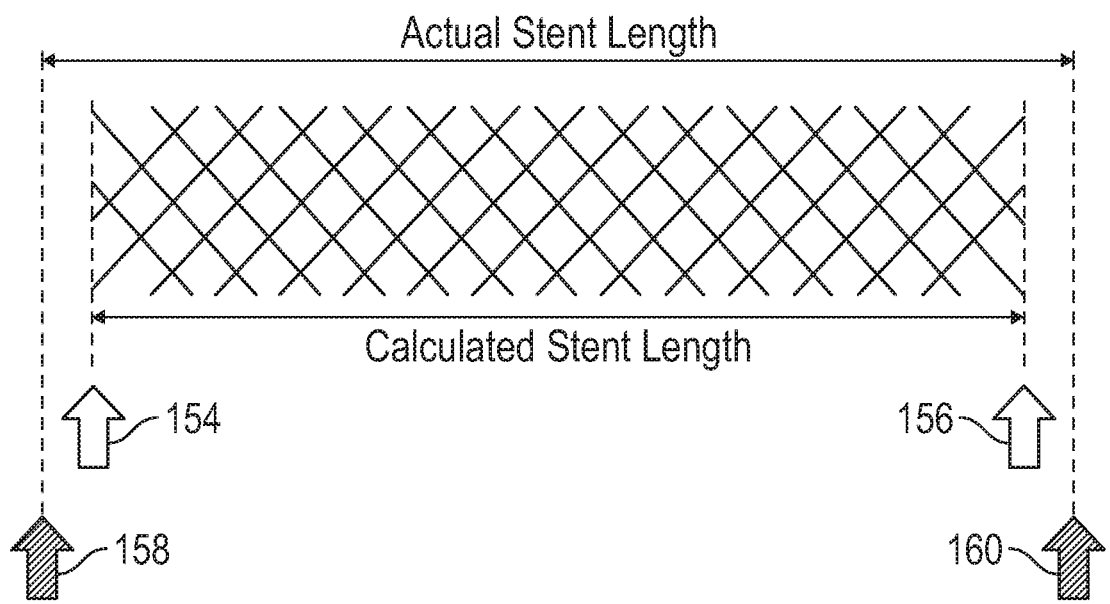

After removing the inappropriate OCT image frames, in step S260, all the OCT image frames in which stent-struts are detected are selected (Group $G_S'$). In step S260 it is determined that the entire range of the stent region in the OCT image is going to be evaluated for stent expansion, but in another embodiment in this step S260 a user may select one or more (first) ranges for evaluating stent expansion, from the stent region where the stent is implanted and the stent-struts are detected. Whether the user selects the first range as the entire range of the stent region or as a partial range of the entire stent region may depend upon system requirements or user needs. In one embodiment, the user may use a mouse device or touch screen device to designate one or more (first) ranges in the stent region, and CPU 70 determines the first range for the stent expansion evaluation. This allows for designation of one or more positions. Subsequently, in step S270, a reference OCT image frame based on the confirmed stented region is selected. FIGS. 10A and 10B are examples of how to select reference frames. If the calculated stent length is equal to or within a predetermined threshold to the actual stent length, the OCT image frame at a position representing the distal end 150 and the OCT image frame at a position representing the proximal end 152 of the stented segment are selected as reference frames as shown in FIG. 10A.

If the calculated stent length is not equal to the actual stent length and not within a predetermined threshold, the reference frames may be selected based on either the calculated stent length or the actual stent length as shown in FIG. 10B. When the calculated stent length is selected for reference frame selection, the OCT image frame at a position representing the distal end 154 and the OCT image frame at a position representing the proximal end 156 of the stented segment are selected as reference frames.

When the actual stent length is selected, in one example, the OCT image frames representing positions (158, 160) that are located at a certain distance from each end of the stented segment may be used as reference frames. The distances to be added at each end can be equal, such as half of the difference between the calculated stent length and the actual stent length. The distances to be added at each end may also be different such as the difference between the calculated stent length and actual stent length is divided differently. In another example, an OCT image frame corresponding to a position representing one end (the proximal or distal end) of the stented segment is selected as one of the reference frames, and an OCT image frame corresponding to a position that is located at a distance equal to the difference between the calculated and the actual stent length from the opposite end of the stented segment is determined as the other reference frame. The choice of how to determine the reference frames in a case where the calculated stent length is not equal to the actual stent length may be set prior to the image processing or set during the PCI procedure.

Figure 11:
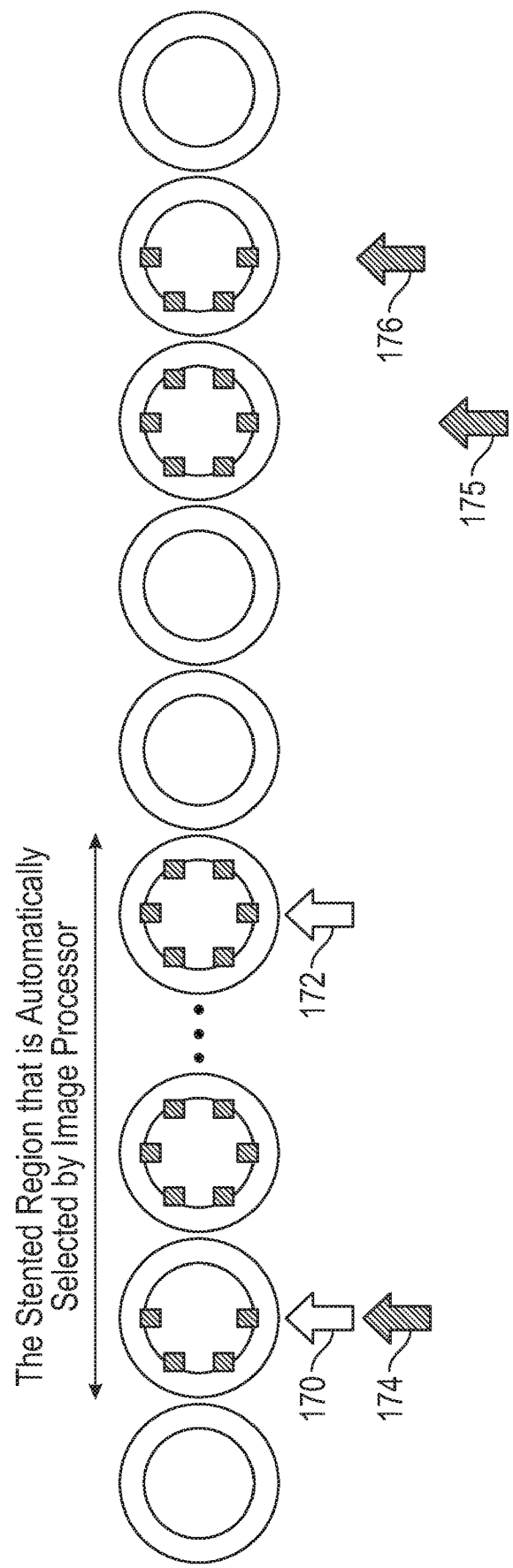
FIG. 11 is a diagram illustrating examples for selecting reference frames for stent expansion evaluation when OCT pullback is affected by cardiac motion in accordance with one or more aspects of the present disclosure.

In the scenario shown in FIG. 7, where the OCT pullback is affected by cardiac motion, the OCT image frames corresponding to positions at the edges of the stent region that the computer automatically selects are selected as reference frames as shown in FIG. 11. The stented region that may be automatically selected by the image processor includes a reference frame corresponding to a position 170 and a reference frame corresponding to a position 172 of the stented region. Selecting positions (170, 172) avoid possible issues associated with an OCT pullback that is affected by cardiac motion.

In another example, the positions (174, 176) corresponding to OCT image frames in which stent-struts are observed most proximally and distally may be used as reference frames also shown in FIG. 11 by the solid arrows. Alternatively, the selection of the reference frames can be modified by a user. Additionally, the user may set certain criteria prior to image processing for selection of the reference frames. The reference area can be an area of an oval that is fitted to the detected stent-struts, the area within the detected lumen edge or a combination of both. Then, the stent expansion is evaluated for each frame in Group $G_S'$. Assuming that the frame number in Group $G_S'$ starts $G_{S'-1}$-th and n frames are in Group $G_S'$. From $G_{S'-1}$-th, stent area is measured and stent expansion is evaluated by comparing the stent area ($A_S$) and the reference area ($A_R$).

$$\text{Expansion [\%]} = (A_S/A_R) \times 100$$

$A_S$ can be the area of the oval that is fitted to the detected stent-struts by straight or slightly curved lines. $A_R$ can be the maximum, minimum or average of the values at two different reference frames. Based on this value, an indicator for stent expansion level is assigned and saved to the corresponding OCT image frame with the evaluated stent expansion value.

Figure 9B:
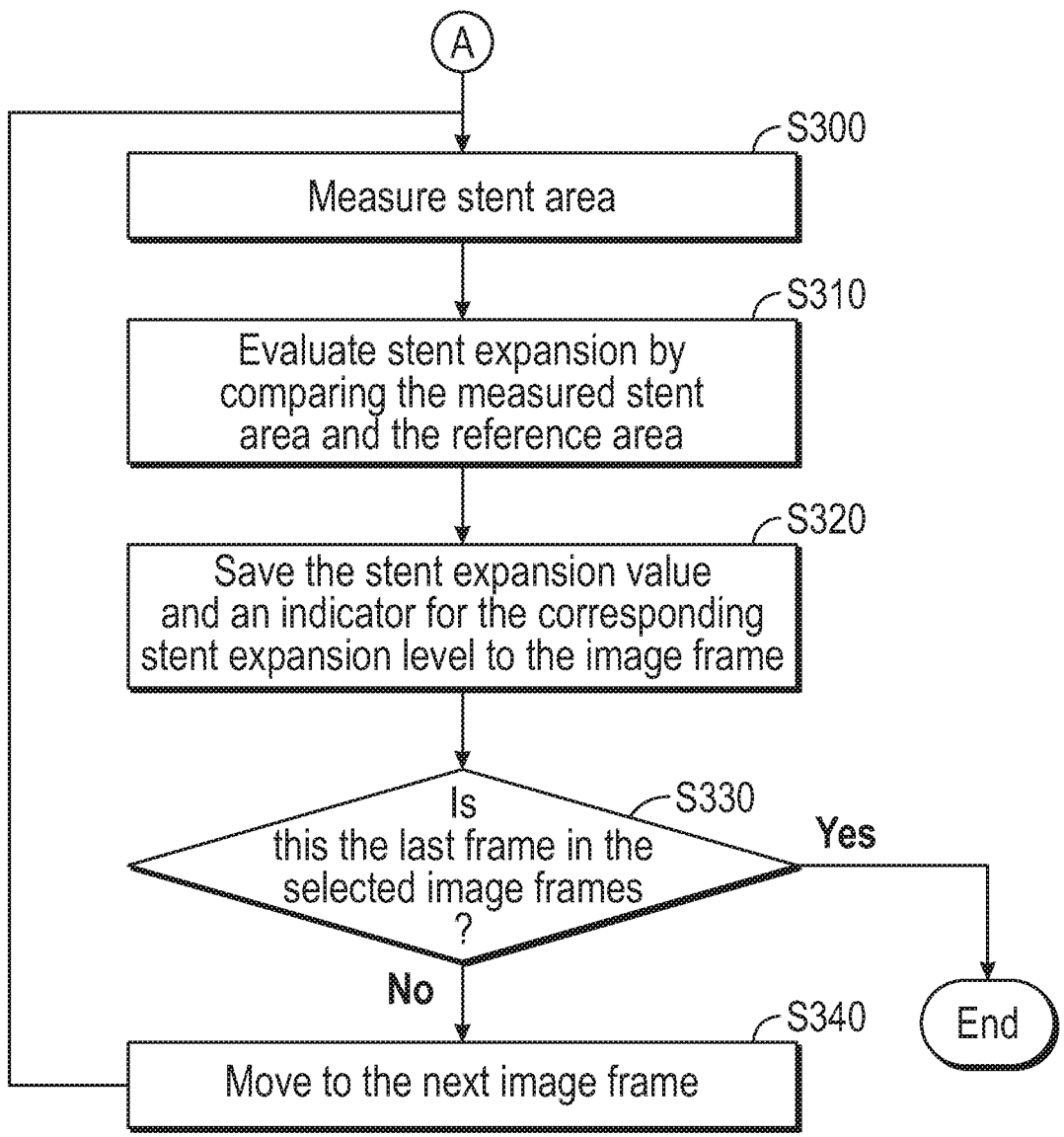

Referring back to FIG. 9A, in step S270 a reference OCT image frame is selected based on the confirmed stented region. Then in step S280, the reference area in the selected reference frame is evaluated. In step S290, the first OCT image frame from the OCT image frames in which stent-struts are detected is selected. Then the stent area is measured for the first OCT image frame in step S300 as shown in FIG. 9B. After measuring the stent area of the first OCT image frame, stent expansion is evaluated by comparing the measured stent area and the reference area in step S310. The stent expansion value and an indicator for the corresponding stent expansion level are saved with the first OCT image frame in step S320. After the stent expansion value is saved, it is determined whether the selected OCT image frame is the last frame in step S330. If the selected OCT image frame is not the last frame (No in step S330) then the next OCT image frame is selected in step S340 and the process returns to step S300. In this example, because the selected OCT image frame is the first OCT image frame, the next frame would be the second OCT image frame from the group of all the OCT image frames in which stent-struts were detected. After selecting the next OCT image frame the process returns to step S300 to measure the stent area for the next OCT image frame. Alternatively, if it is determined in step S330 that the selected OCT image frame is the last frame (Yes in step S330), then the process for evaluating stent expansion is completed for the acquired OCT image. According to this workflow, every OCT image frame in which stent-struts are detected and not affected by artifact is processed to obtain a stent expansion value based on the stent area associated with a selected OCT image frame and a reference area. The reference area remains the same for each OCT image frame from the OCT image frames in which stent-struts are detected and not affected by artifact.

Figure 12:
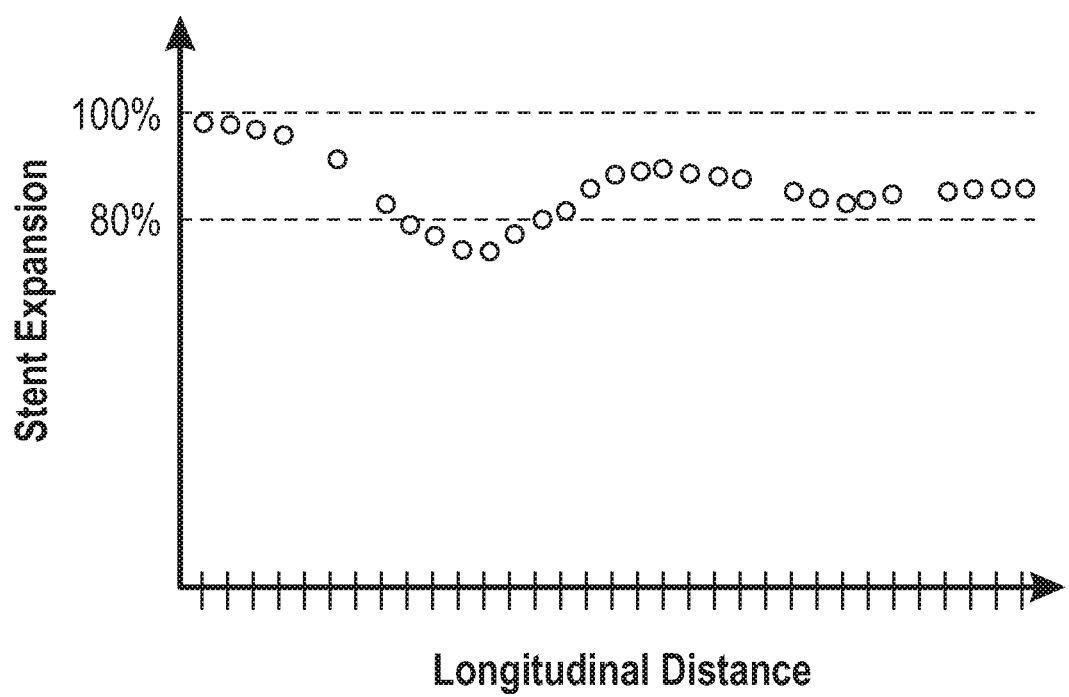
FIG. 12 is a graph illustrating an exemplary results for evaluating stent expansion

FIG. 12 is one example of results of the stent expansion evaluation in a graph form. The x-axis corresponds to the longitudinal distance of the OCT pullback and the y-axis corresponds to the evaluated stent expansion value. Each mark on the x-axis refers to each OCT image frame in which stent-struts were detected and the corresponding stent expansion value. As shown in FIG. 12, since the stent expansion is evaluated for each OCT image frame, the values are discrete and each value corresponds to each OCT image frame. If there is one or multiple frame(s) in which stent expansion is not evaluated, the value will not be shown on the corresponding frame. A user viewing the graph is able to determine where the stent expansion value falls below a certain threshold such as 80% for example. The user may also determine where stent expansion is sufficient based on viewing the graph.

Figure 13A:
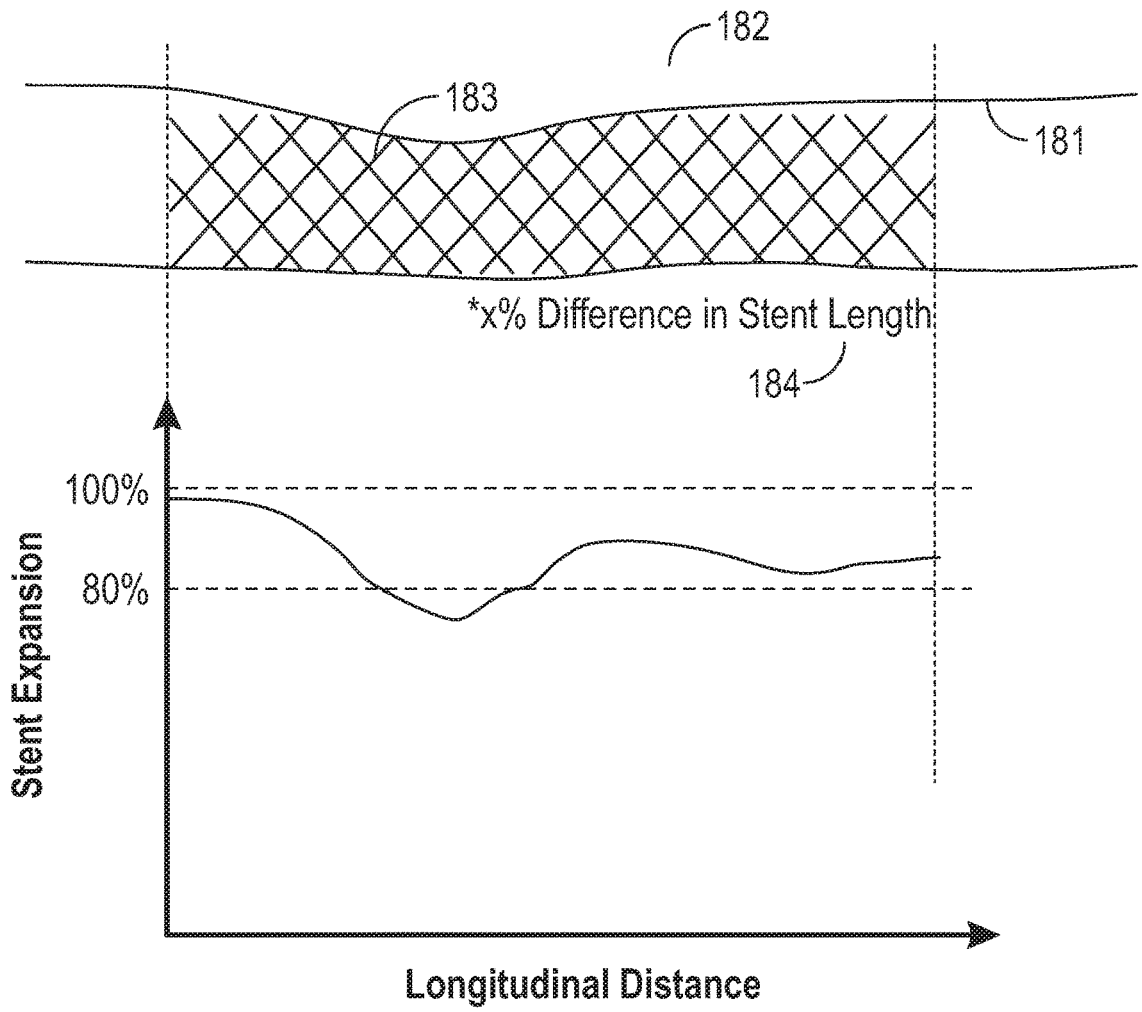
FIG. 13A is a diagram illustrating stent expansion evaluation results including a longitudinal view with a graph below to be displayed on a display unit in accordance with one or more aspects of the present disclosure.

Once stent expansion evaluation is completed, the results may be displayed on a monitor. Referring now to FIG. 13A, the stent expansion value is shown as a graph 180 underneath the longitudinal view 182, which is created from the OCT pullback. The longitudinal view 182 of the stented segment includes the lumen borders 181 as well as the stent-struts 183 that form the stented region. In this case, a user can interpret the stent expansion value along a range of the stented segment in the longitudinal direction. In the graph shown in FIG. 13A, the user may recognize that the area in the graph where the stent expansion value falls below 80% is an area where stent underexpansion may exist by way of example.

Figure 13B:
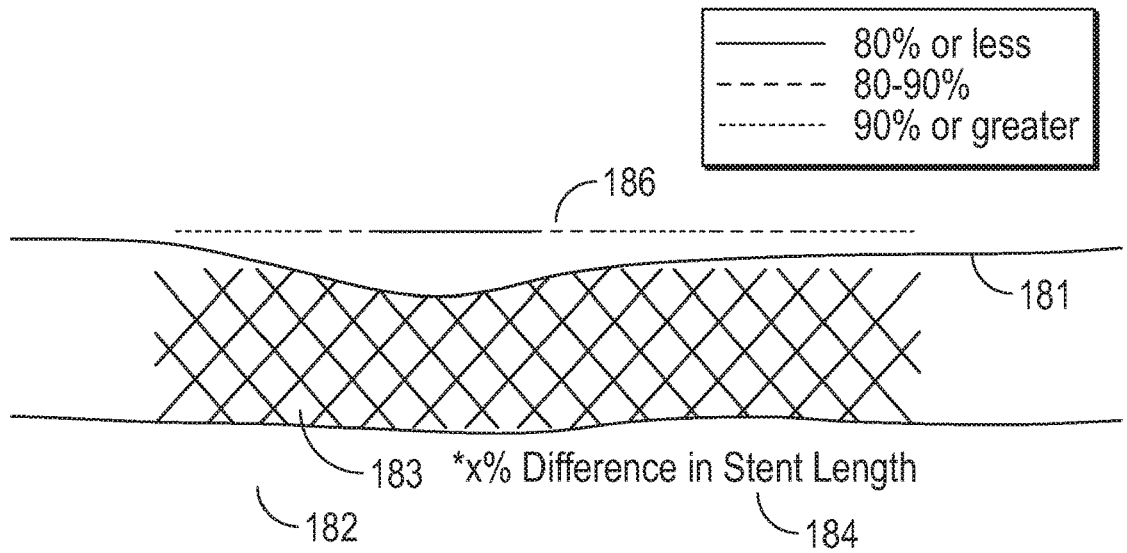
FIG. 13B is a diagram illustrating an indicator along a range of the stented segment for evaluating stent expansion levels in accordance with one or more aspects of the present disclosure.

In FIG. 13B, the stent expansion is shown by an indicator 186, which may enable a user to more readily interpret the level of stent expansion. For example, in step S120, the CPU 70 generates a stent expansion indicator. The indicator 186 could be two or three levels and the range of each level may be preset or modified by a user. The indicator in FIG. 13B is a three level indicator. Each level associated with the indicator refers to a range of stent expansion values. For example, a first level may refer to a range of stent expansion values that are 90% or greater which may correspond to good stent expansion. A second level may refer to a range of stent expansion values that are between 80% and 90% which may refer to sufficient stent expansion. A third level may refer to a range of stent expansion values that are below 80% which may refer to insufficient stent expansion or stent underexpansion. The indicator 186 may be color coded for example, where a green color represents a first level, yellow color represents a second level and red color represents a third level. In one embodiment of the stent expansion indicator generation, each valid stent expansion value, corresponding to a two-dimensional image frame of the acquired OCT image, is mapped to a specific color which represents the level of the stent expansion value. This mapping is performed based on each stent expansion value and a criterion value, which is for example 80% or 90% as explained above. In FIG. 13B the indicator 186 is represented by dotted lines, solid lines and semi-solid lines where the dotted lines represent the first level, the semi-solid lines represent the second level and solid lines represent the third level. In FIG. 13B, the solid line indicates a (second) range where the underexpansion has occurred. This second range is within the (first) range where the stent expansion is evaluated. In a different case the indicator may indicate two or more (second) ranges where the underexpansion has occurred. Alternatively, if the indicator is two levels, the first level may represent sufficient stent expansion and the second level represents a range of stent expansion that is insufficient or considered stent underexpansion. In both FIGS. 13A and 13B, the difference between the actual stent length and the calculated stent length 184 is shown underneath the longitudinal view 182 of the OCT pullback so that the user is aware of the quality of OCT pullback. For example, the smaller the difference in stent length the greater the quality of OCT pullback. The larger the difference in stent length the lower the quality of OCT pullback.

Figure 14A:
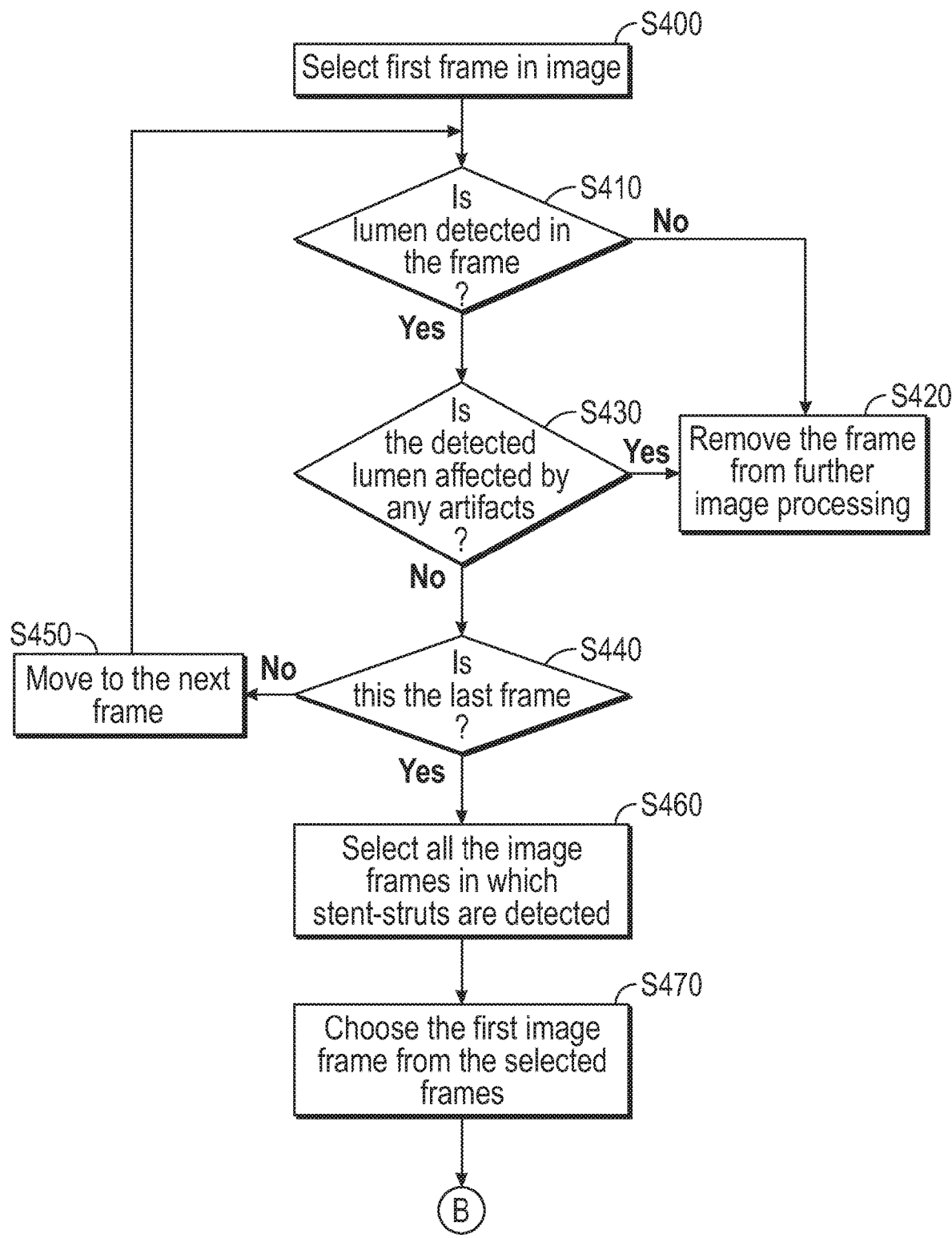
FIGS. 14A and 14B are workflows for evaluating stent apposition in accordance with one or more aspects of the present disclosure.
Figure 14B:
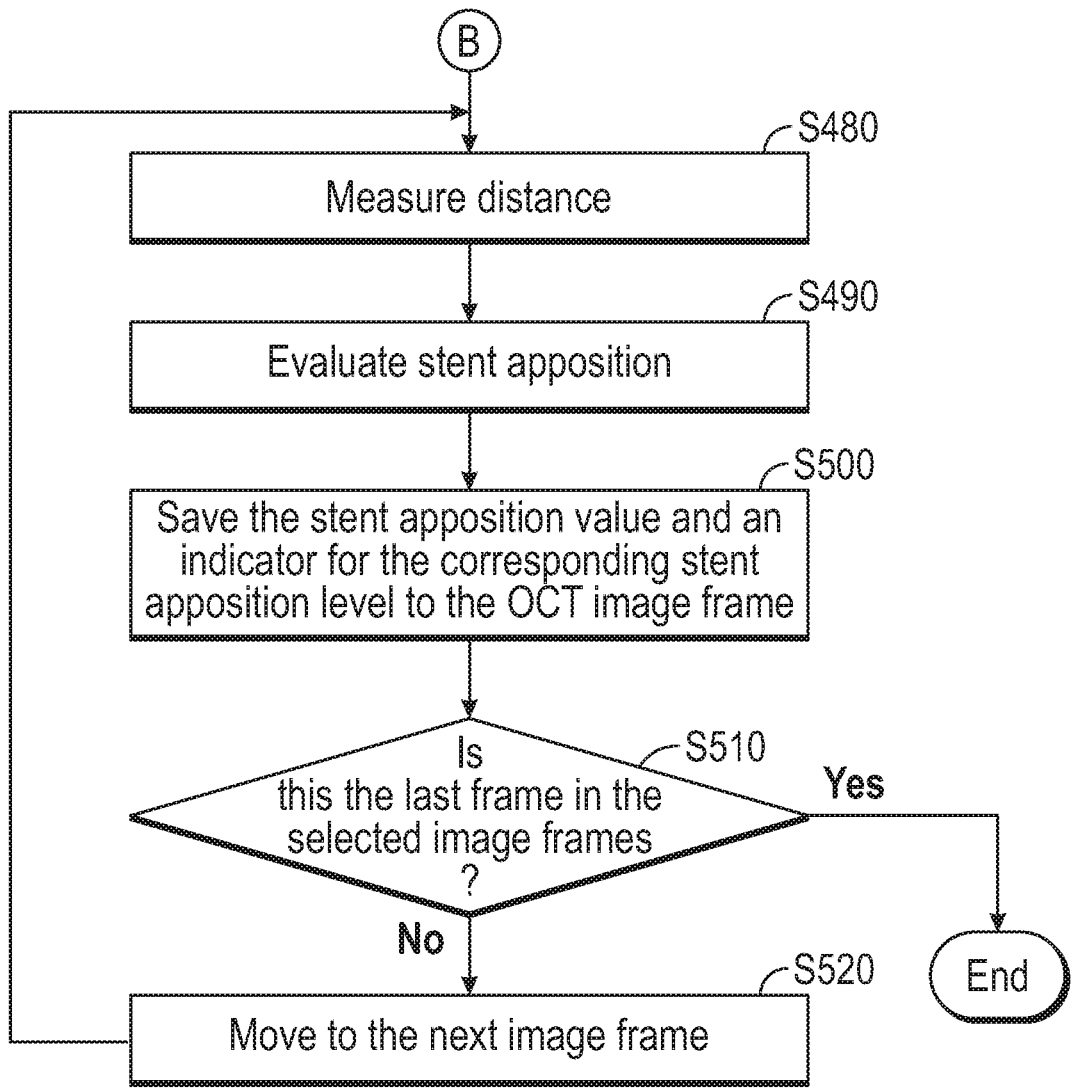

FIGS. 14A and 14B are exemplary flowcharts illustrating various steps for evaluating stent apposition. Steps S400 through S460 of FIG. 14A are similar to steps S200 through S260 of FIG. 9A and will not be repeated herein. In step 470, a first OCT image frame from the selected OCT image frames in which stent-struts are detected is selected. Subsequently in step S480, for the selected first OCT image frame, the distance between the lumen edge and stent-strut detected in first OCT image frame is measured. In step S490, stent apposition is evaluated. The stent apposition is evaluated by comparing the measured distance between the lumen edge and stent-strut to the stent-strut width that is obtained from the stent information. In step S500, the stent apposition value and an indicator for stent apposition level is saved for the corresponding OCT image frame. In step S510, it is determined whether the selected OCT image frame is the last OCT image frame, if the selected frame is the last frame (Yes in step S510) then the process ends. In this example the selected OCT image frame is the first OCT image frame, so a second OCT image frame is selected in step S520 and the process returns to step S480. The process repeats until each OCT image frame selected in step S460 is evaluated and a stent apposition value is obtained.

In one example, stent apposition is evaluated by comparing the representative distance of the frame, such as a maximum, minimum or average distance of all the evaluated distance in the frame, to the actual stent-strut width. In another example, stent apposition is evaluated as the percentage of stent-struts that have a greater distance than the actual stent-strut width in the frame.

Figure 15:
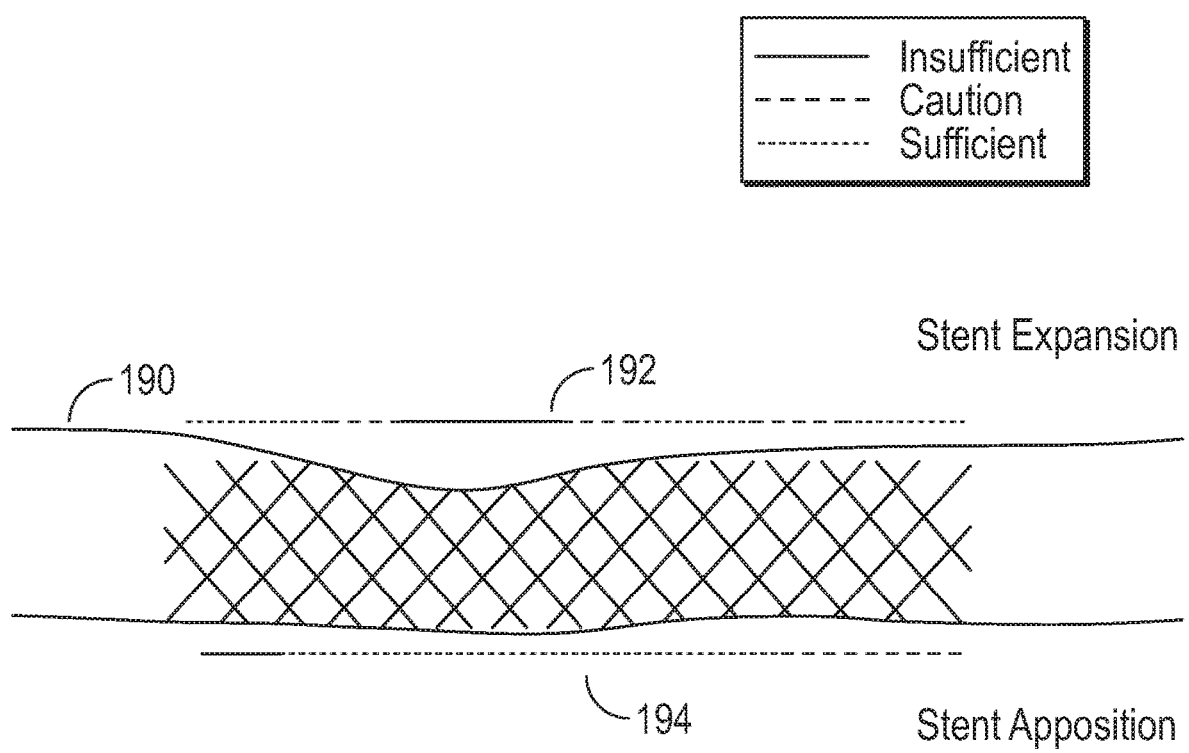
FIG. 15 is a diagram illustrating an exemplary way of displaying stent expansion levels and stent apposition levels simultaneously in accordance with one or more aspects of the present disclosure.

FIG. 15 illustrates an example of how to display stent expansion and stent apposition together with the longitudinal view 190 of the OCT pullback. Similar to the stent expansion indicator 192, the indicator 194 for stent apposition may include three levels or two levels. Once the stent apposition is evaluated for all the OCT image frames in Group Gs', the stent apposition result can be displayed on a monitor in the same manner of the stent expansion result.

The indicator for both stent expansion and stent apposition in FIG. 15 is a three level indicator representing a sufficient status, an insufficient status, and a caution status by way of example.

Figure 16A:
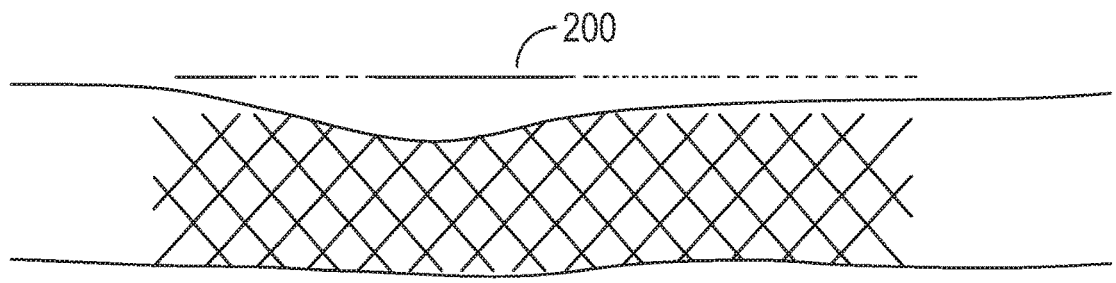
FIG. 16A is a diagram illustrating an indicator with three different levels for navigating further intervention in accordance with one or more aspects of the present disclosure.
Figure 16B:
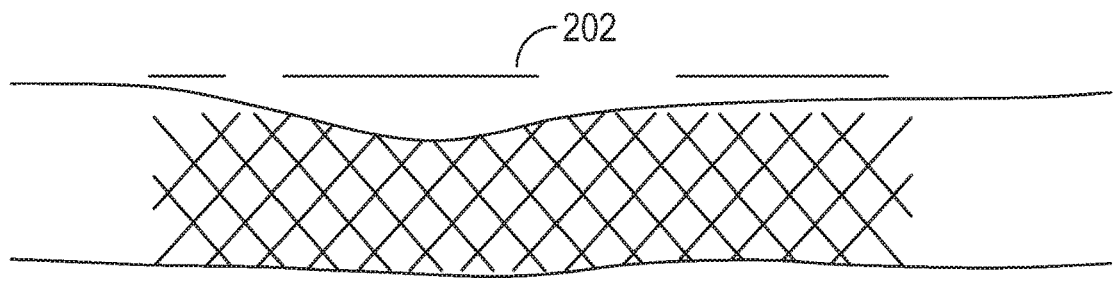
FIG. 16B is a diagram illustrating an indicator with two different levels for navigating further intervention in accordance with one or more aspects of the present disclosure.
Figure 16C:
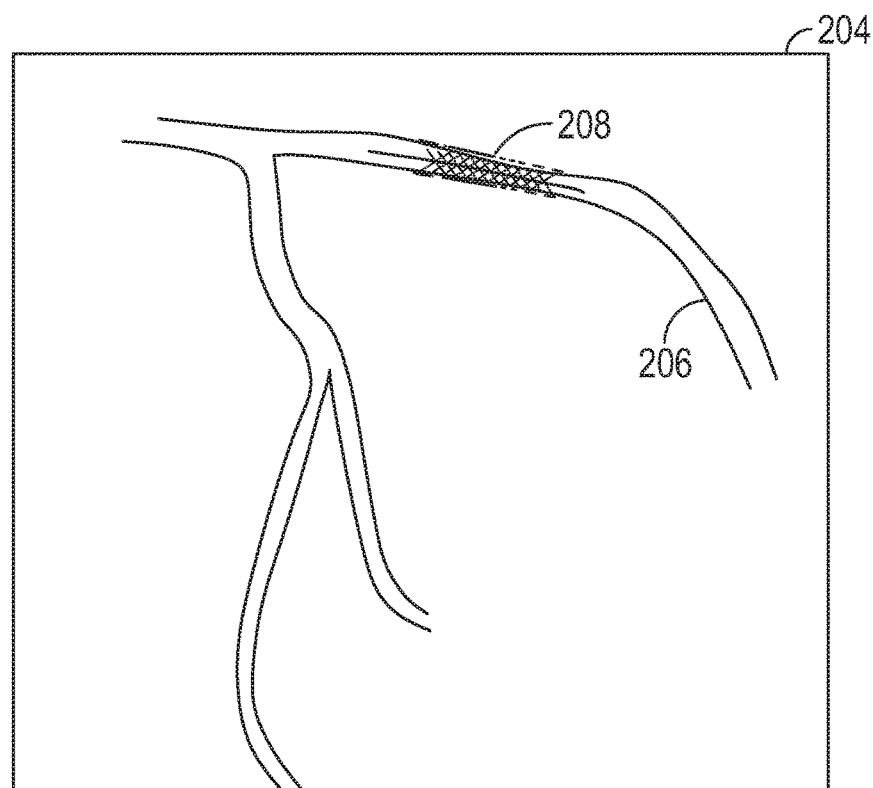
FIG. 16C is a diagram illustrating an angiography image co-registered with an OCT image for evaluating stent expansion and stent apposition and for navigating further intervention in accordance with one or more aspects of the present disclosure.

Referring now to FIGS. 16A-C, the image processor may generate a new single indicator for a physician to navigate a further interventional procedure. One such example of a single indicator includes an indicator for post-dilation. As described in Table 1, there are multiple post-stenting statuses. The goal is make sure that the entire stented segment is sufficiently expanded and well-apposed. To achieve this goal, the implanted stent may be post-dilated. FIGS. 16A-C illustrate several examples for displaying the post-dilation indicator. The post-dilation indicator 200 may include three levels as shown in FIG. 16A or two levels as shown by the indicator 202 in FIG. 16B. In another example, the information can be shown in fly-through view or three-dimensional (3D) rendering view that is created from the acquired OCT pullback. If the OCT image is coregistered with an angiography image, the indicator 208 may be displayed on an angiography image frame 204 including the vessel 206 as illustrated in FIG. 16C. A user may view the stented region within the vessel in the angiography image 204. The coregistration may be performed with any available methods.

Figure 17:
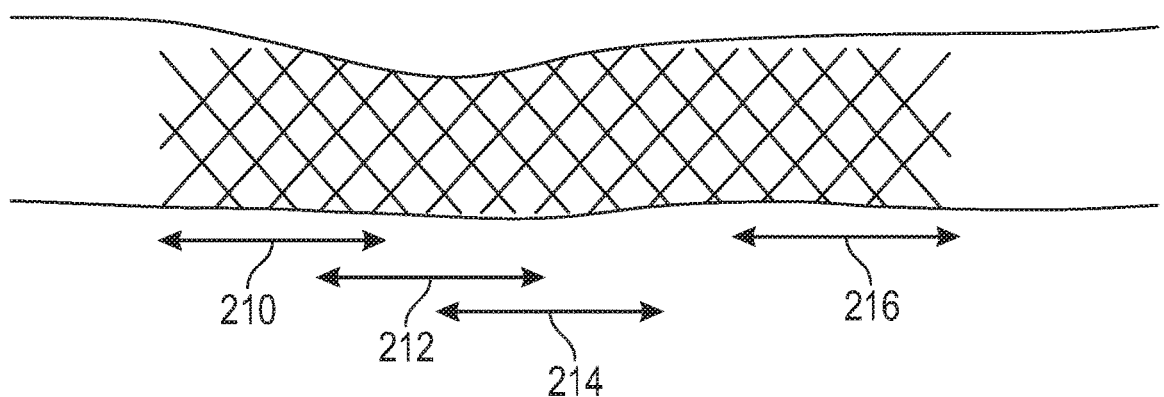
FIG. 17 is a diagram illustrating an exemplary way for navigating post-dilation procedure in accordance with one or more aspects of the present disclosure.

Another example of a single indicator is illustrated in FIG. 17. The single indicator in FIG. 17 is a navigator for balloon location for post-dilation. Post-dilation is typically performed with a balloon whose length is shorter than that of the original balloon for stenting, thus multiple dilations are required. The double-sided arrows (210, 212, 214, 216) in FIG. 17 illustrate where the balloon for post-dilation should be placed. To generate this indicator (210, 212, 214, 216), the longitudinal length of the post-dilation area is divided by the length of post-dilation balloon considering a certain overlap of the balloon locations (e.g., 2-4 mm) and a certain margin at the edge of post-dilation area (e.g., 2-4 mm). This may be generated based on the balloon information that a physician is planning to use, which is entered into the system by a nurse or technician during a procedure. The indicator may be generated based on the preset post-dilation balloon information. The indicator may also be generated based on the image processor suggestion with a suggestion for balloon type and size (diameter and length). The diameter of the post-dilation balloon can be determined based on the diameter at the reference frames, which can be calculated from the reference area $A_R$. The length can be determined to minimize the number of post-dilation.

Figure 18:
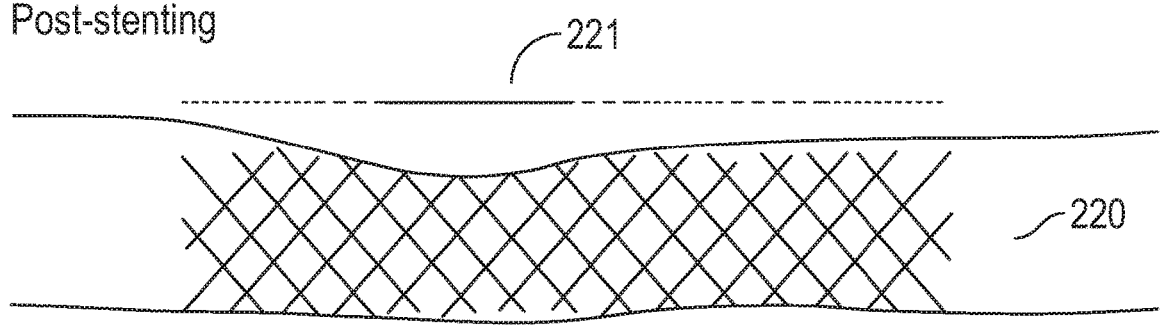
FIG. 18 is a diagram illustrating a display of post-stenting OCT and post-dilation OCT.

If another OCT pullback is acquired after post-dilation, the comparison before and after post-dilation may be displayed on a monitor as illustrated in FIG. 18. By displaying the longitudinal view 220 of the vessel before dilation (post-stenting) and the longitudinal view 222 after post-dilation, a physician may better understand how to improve the post-stenting status. The indicator 221 for stent expansion post-stenting still includes ranges where stent under-expansion remains. However, a physician may use the indicator 221 to improve stent expansion as shown by the indicator 223 post-dilation. In this comparison, the location of the stent in the longitudinal direction is aligned for easier interpretation.

In another embodiment of the present disclosure, stent expansion may be evaluated every other OCT image frame or every few frames. That number of frames that are skipped may be preset or selected by a user. Stent apposition evaluation may be performed in the same manner.

In another embodiment of the present disclosure, the reference area $A_R$ can be determined for each OCT image frame in Group $G_S'$ based on the reference areas at proximal and distal edges. Consider $A_{RP}$ and $A_{RD}$ as the reference areas at proximal and distal edges, respectively. For i-th frame of Group $G_S'$, the reference area $A_R$ is calculated as follows:

$$A_{Ri} = A_{RD} + w_i \times (A_{RP} - A_{RD})$$

where $0 \leq w_i < 1$

If the reference area $A_{Ri}$ is linearly interpolated, $w_i$ will be $$w_i = i/N$$

where N is number of frames in Group $G_S'$

In another embodiment of the present disclosure, stent expansion or apposition evaluation may be interpolated for the OCT image frames that are included in Group $G_S$, but not included in Group $G_S'$, if the number of frames that are continuously excluded in Group $G_S'$ is less than a threshold amount of frames. The threshold amount of frames may be preset. A user may also modify the threshold amount before or during the PCI procedure.

In one of the above-described embodiments, for determining the distributed positions for evaluating stent expansion, some OCT frames are eliminated before the calculation of stent expansion values, as shown in FIG. 12 and in Steps S230 and S220, in order to make all of the calculated expansion values valid. But in another embodiment, stent expansion values are calculated at all of the image frames of the intravascular image, where the lumen border and stent-struts are detected. In this embodiment there is a determination process if the detected lumen is in the frame or not, as shown in step S210, and a determination process if the detected stent-strut is in the frame or not, as shown in step S260. But there is not a determination process if the detected lumen is affected by any artifacts or not, shown in step S230. In this embodiment, the CPU 70 determines whether or not each of the stent expansion values calculated at an OCT image frame is valid, after the calculation of stent expansion value. This process may be performed between steps S310 and S320. In this embodiment the determination process of the distributed positions for evaluating stent expansion, is checking if the stent-strut is detected and if the lumen border is detected at each image frame for selecting appropriate image frames, in order to make the calculation successful, but not to assure the validity of the stent expansion value. The validity of the stent expansion is checked after the stent expansion value calculation, as described above.

The determination results as to whether each of the stent expansion value is valid or not, may be used by CPU 70 to display the stent expansion indicator 192 (or 186, 200, 202, 208, 210, 212, 214, 216, 221, 223—hereinafter in this paragraph, '192' for short). In one embodiment the stent expansion value which is not valid is not displayed. In other words the CPU 70 does not create the stent expansion indicator 192 (or 186, 200, 202) to be displayed, for the invalid expansion value calculated from a certain image frame. In another embodiment, the CPU 70 sets, for the stent expansion indicator 192, a different color for the invalid expansion value, from the colors for the valid expansion values. For example, if red, yellow and green are used for the valid expansion values, grey or blue is used for the invalid expansion values, for users to understand which expansion value is determined as valid and which expansion value is determined as not valid.

In one of the above-described embodiments, CPU 70 may determine where the stent expansion value falls below a certain threshold such as 80% for example, as shown in FIG. 12. But in another embodiment, CPU 70 may determine that stent underexpansion has occurred if a value for evaluating stent expansion is above a certain threshold by defining a different value for stent expansion. One example of the different value can be:

$$(A_R - A_S)/A_R \times 100$$

In another embodiment, CPU 70 may determine whether stent expansion occurs or not by evaluating the ratio of the evaluated stent expansion value to the threshold value. For example, if stent expansion is evaluated as Expansion[%]= $(A_S/A_R) \times 100$, when a ratio, Expansion/threshold, is equal to or less than 1, it can be considered that stent underexpansion has occurred at the location where stent expansion value is evaluated.

Figure 19:
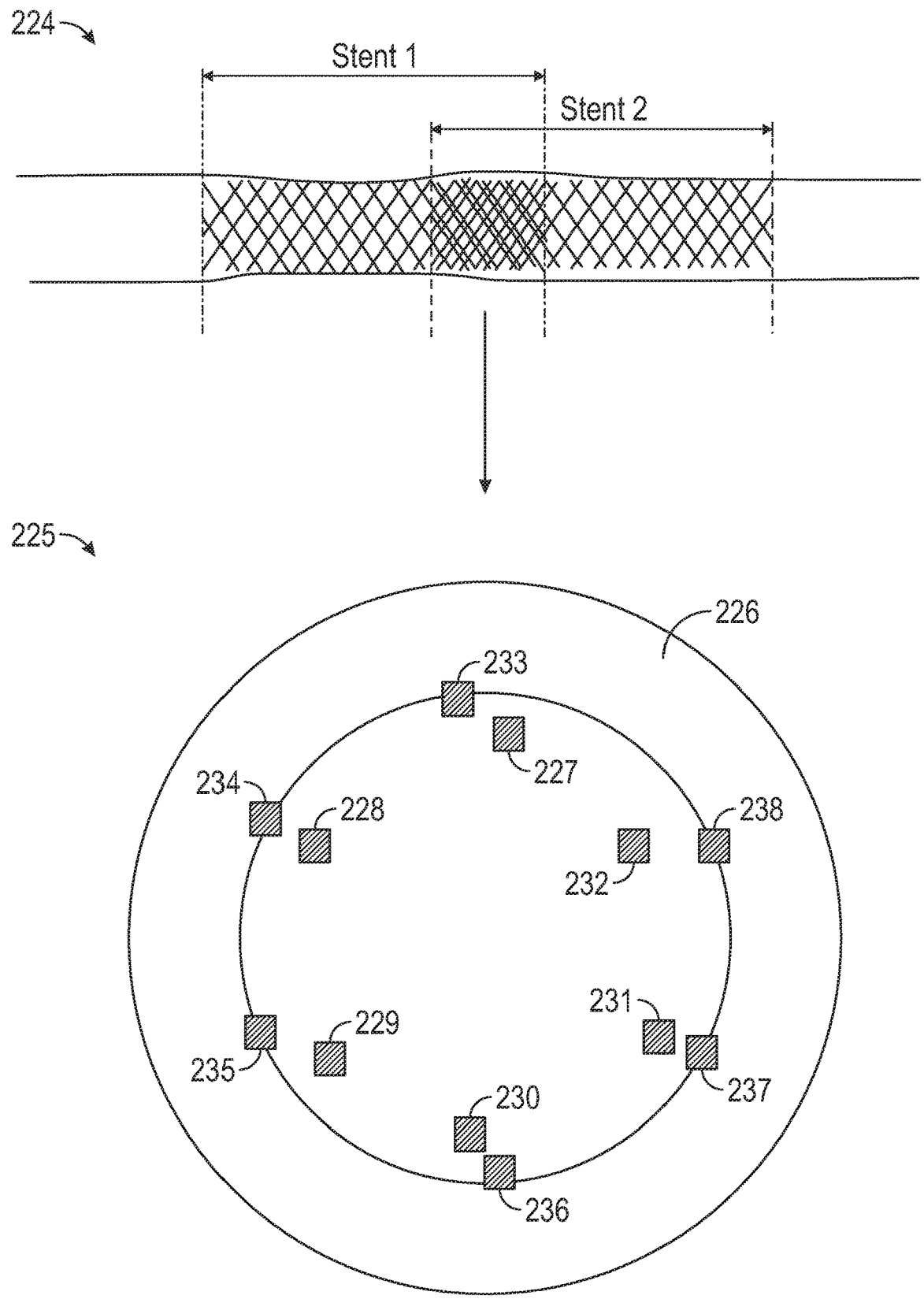
FIG. 19 is a diagram illustrating partially overlapped stents in a longitudinal direction and a cross-sectional view.

FIG. 19 includes both a longitudinal view of a stented segment 224 and a cross-sectional view 225 of the stented segment 224. The stented segment 224 includes two stents that partially overlap (Stent 1 and Stent 2). The cross-sectional view 225 of lumen 226 for the partially overlapped stented segment 224 includes reference numerals 233-238 which represent Stent 1 and reference numerals 227-232 which represent Stent 2. In the case where two or more stents are implanted with partial overlap, the CPU 70 evaluates stent expansion and malapposition in the overlapped region using the detected stent-struts that are located innermost of the lumen (Stent 2, 227-232).

In the above-described embodiments shown in FIGS. 13B, 15, 16A-C, 17 and 18, the stent expansion indicator 192 (or 186, 200, 202, 208, 210, 212, 214, 216, 221, 223—hereinafter in this paragraph '192' for short) is displayed with a vessel image, for example a longitudinal view of the OCT image or an X-ray angiography image, or a combination of these vessel images. In another embodiment, the stent expansion indicator 192 is displayed with an image, for example a luminogram that shows a lumen diameter in the longitudinal direction. The stent-struts can be modeled in this image based on the distance from lumen border and stent-struts. The image may include an entire range in which the stent is implanted, for user's understanding of stent expansion in an entire range of the implanted stent.

Figure 20:
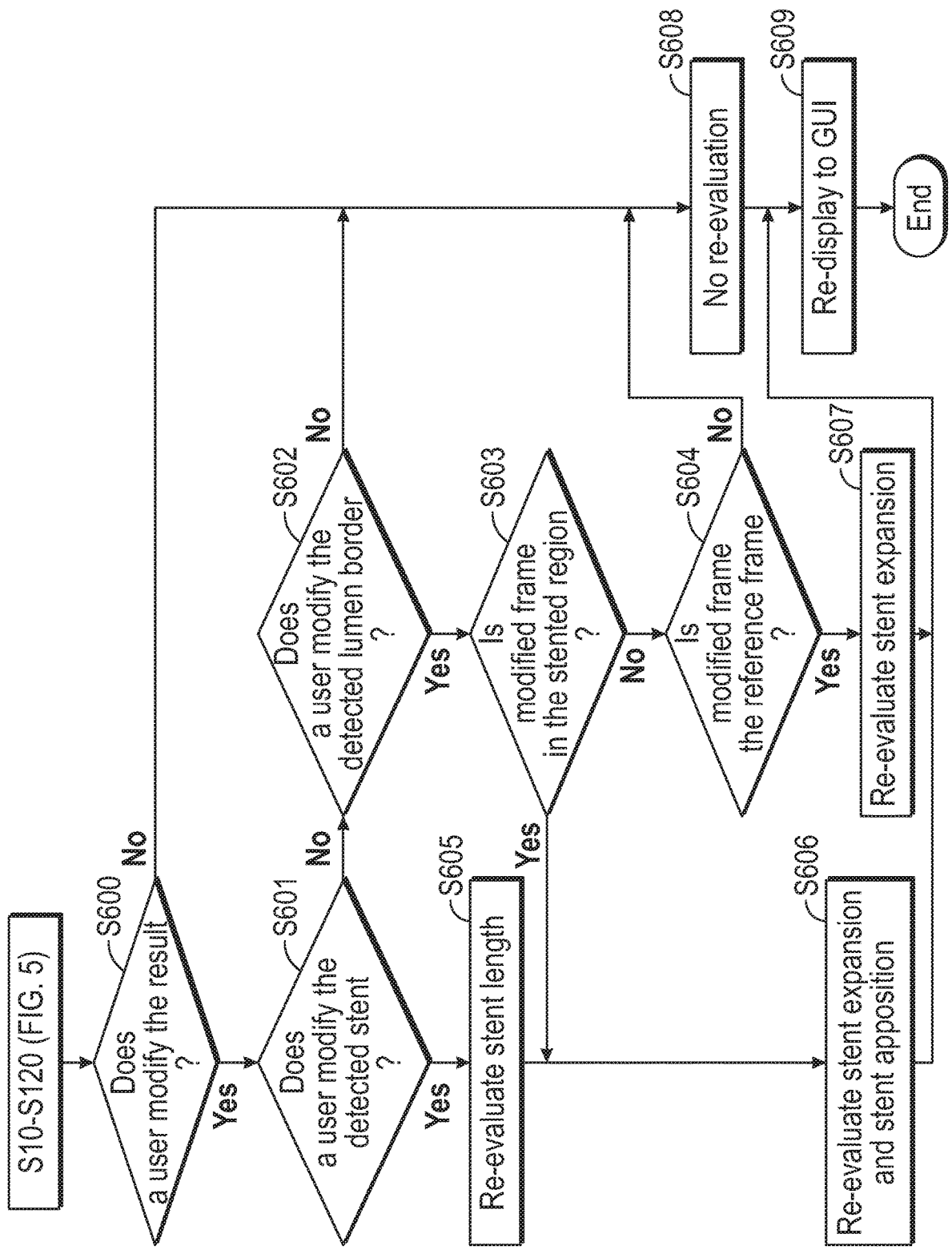
FIG. 20 is a flowchart illustrating a workflow of re-evaluating stent expansion and stent apposition after a user modification of a detected result in accordance with one or more aspects of the present disclosure.

Referring now to FIG. 20, a workflow for re-evaluating stent expansion and stent apposition after a user modifies the detected result is shown. The user modification may occur after steps S10-S120 in FIG. 5 are completed. In step S600 of FIG. 20, it is determined whether a user modified the detected result(s) of lumen and/or stent. If the user has modified the detection results (Yes in step S600), it is then determined if the user has modified the detected result(s) of the stent in step S601. If the user modifies the detected result(s) of the stent (Yes in step S601), the CPU 70 re-evaluates the stent length in step S605 as well as re-evaluating both stent expansion and stent apposition in step S606. After re-evaluating both stent expansion and stent apposition, the CPU 70 displays the re-evaluated result on the GUI in step S609.

Referring back to step S601, if it is determined that the user does not modify the detected result(s) of stent (No in step S601), then it is determined whether the user modified the detected lumen border in step S602. If the user has modified the detected lumen border (Yes in step S602), the CPU 70 checks where the frame(s) that the user modified are located. In step S603 it is determined whether the modified frame(s) is located in the stented region. If the modified frame(s) is in the stented region (Yes in step S603), the CPU 70 re-evaluates both stent expansion and stent apposition in step S606. If it is determined in step S603 that the modified frame(s) is not in the stented region, then it is determined in step S604 if the modified frame(s) is the reference frame(s). If it is determined that the modified frame(s) is the reference frame(s) (Yes in step S604), then the CPU 70 re-evaluates stent expansion in step S607. If the modified frame(s) is not in the stented region (No in step S603) or the reference frame(s) (No in step S604), then the CPU 70 does not perform any re-evaluation in step S608.

Figure 21:
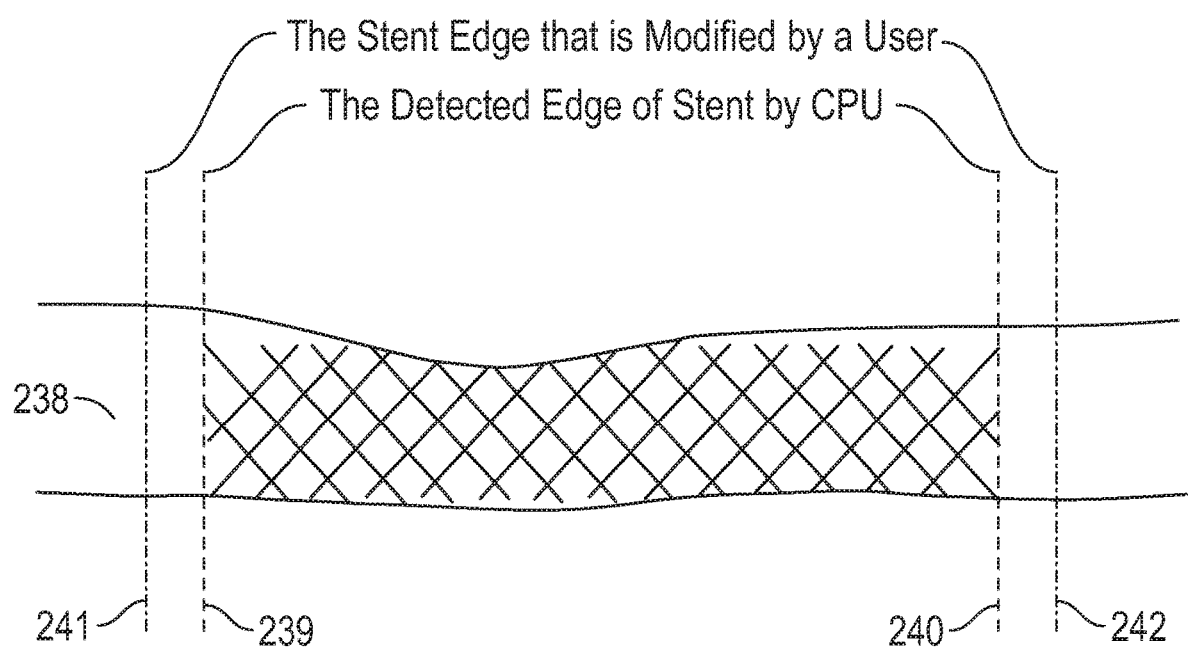
FIG. 21 is an exemplary diagram illustrating user modification of a detected stented region in the longitudinal view.

The user may modify the detected stent in either the longitudinal view or the cross-sectional view. The re-evaluation of stent expansion and stent apposition may differ based on how the user modifies the detection results. FIG. 21 illustrates the case where the user modifies the detected stented region in the longitudinal view of the lumen 238 such that the detected stent edges (239, 240) are moved outside of the area where the CPU 70 detected the stented region. Edges (241, 242) represent the stent edge that is modified by the user. In this example the CPU 70 re-defines the reference frames. This process may be performed in a similar manner based on the methods described with reference to FIGS. 10A and 10B. CPU 70 may request a user to manually select the reference frames. The CPU 70 may also show a notification requesting that a user check any stent-struts that are not detected by the CPU 70 in the cross-sectional views in the areas between 239 and 241 and the areas between 240 and 242. If the user identifies any stent-struts in any of those frames, the CPU 70 evaluates stent expansion and stent apposition, and displays the results on the GUI as previously described. For the frames that are located in these areas but a user is unable to identify any stent-struts, the user may select whether CPU 70 performs an interpolation of stent expansion and stent apposition evaluation for those frames and display the interpolation on the GUI, displays an alert on the GUI, or does not display any result or alert in the GUI. In this example, the user modifies the locations for both stent edges, but CPU 70 performs the same process if the user changes only one stent edge.

If the user modifies the detected stent edges to within the detected stent region, the CPU 70 may request the user to select which frame(s) to be used as a reference frame(s). The user may select a reference frame(s) in the same manner as described with reference to FIGS. 10A and 10B, or can select using the same reference frame(s) that were originally selected by the CPU 70. If the user selects different reference frame(s), the CPU 70 re-evaluates stent expansion and stent apposition for the frames within the modified stent edges and displays the result. The CPU 70 does not display any stent expansion or stent apposition information for the frame(s) that is located within the detected stent edges and the modified stent edges. If a user prefers, the CPU 70 may select not to display or to change the color of the stent-struts that are detected on the frames that are located between the CPU 70-detected stent edge and the user-modified stent edge. This selection may be made as a default setting during the procedure and/or for post-procedure review, or can be made by a user at any time.

Figure 22:
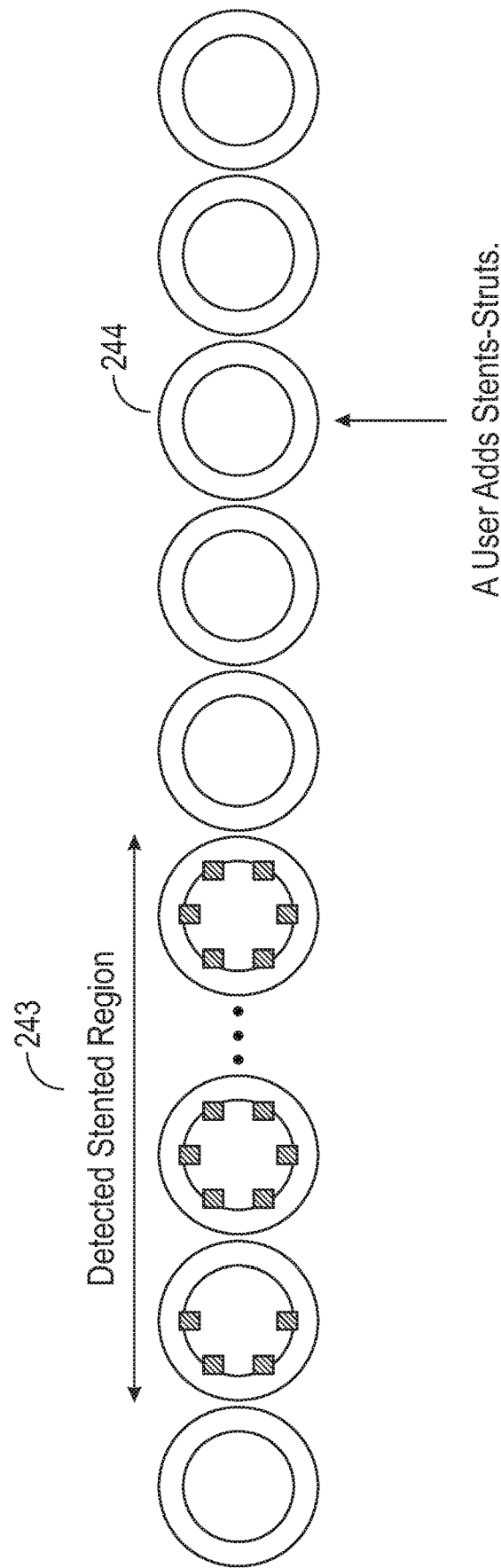
FIG. 22 is a diagram illustrating how a user modifies the detected stent-struts in the cross-sectional view and location of the modified frame relative to the detected stented region.

In FIG. 11 with 170 and 172 as the CPU detected stent edges, if a user modifies the stent edges as 174 and 176, the CPU 70 re-evaluates stent expansion and stent apposition for the frame(s) in which CPU 70 detects the stent-struts (the frames between 175 and 176) and displays the results on the GUI. For the frame(s) in which the CPU 70 did not detect any stent-struts, the user may select whether the CPU 70 performs an interpolation for those frames and display it on the GUI, displays an alert on the GUI, or does not display any result or alert on the GUI. Additionally, assuming that the user modifies the detected stent-struts in the cross-sectional view. If the user identifies stent-struts and adds them in a modified frame(s) 244 as shown in FIG. 22 that is located outside the stented region 243, the CPU 70 may perform the same process that is described above with respect to the case when the user modifies the detected stent edge(s) outside the detected stented region. If the user prefers to extend the stented region 243 to include modified frame 244, the CPU 70 may re-check whether stent-struts are detected in the frame(s) that is located between the originally detected stented region 243 and the modified frame 244. If the CPU 70 cannot identify any other stent-struts in the frame(s), CPU 70 can decide whether to interpolate and display based on a user preference.

If the user identifies stent-struts and adds them in a frame(s) that is located outside the detected stented region but that is located continuously from the detected stented region, CPU 70 re-defines the reference frame(s) in a similar manner that is described above when the frame(s) are outside the detected stented region, re-evaluate stent expansion and stent apposition, and display the re-evaluated results on the GUI.

If a user identifies additional stent-struts and adds them in a frame(s) that is located within the detected stented region, CPU 70 re-evaluates stent expansion and stent apposition using the reference frames that are already defined previously, and display the re-evaluated result on the GUI. If the modified frame(s) is the frame that was not included for evaluation of stent expansion and stent apposition because it did not satisfy the criteria based on the examples shown in Table 2, but if the frame satisfies the criteria after the user modification, CPU 70 re-evaluates stent expansion and stent apposition and, the re-evaluated result is displayed on the GUI after re-evaluating stent expansion and stent apposition.

If the user removes the detected stent-struts, the CPU 70 determines whether the modified frame(s) still meets the criteria to be included in the stented region. In addition, CPU 70 determines where the modified frame(s) is located. If the modified frame(s) meets the criteria and if the frame is not located at the edge of the stented segment, CPU 70 re-evaluates stent expansion and stent apposition and displays the result on the GUI. If the modified frame(s) does not meet the criteria and if it is not located at the edge of the stented segment, the modified frame(s) is excluded from the evaluation of stent expansion or stent apposition. The user may select to keep display of the previous result on the GUI, interpolate from the other frames and display the updated result on the GUI, or not display the result for the modified frame(s). If the modified frame(s) does not meet the criteria and if it is located at the edge of the stented segment, CPU 70 re-defines the reference frame(s), re-evaluates stent length and stent expansion and stent apposition for all the frames that are included in the stented region, and displays the re-evaluated results on the GUI.

Referring now to FIG. 23, an exemplary embodiment in which two stents are implanted is shown. Although FIG. 23 shows only two stents, the methods applied in FIG. 23 may also be applied for cases where more than two stents are implanted. In FIG. 23, two stents are implanted without any overlap. If a user modifies the detected stent-struts in the frame(s) that is located within 246 and/or 247 or within the detected stented region 248 or 249, the CPU 70 performs the same process described above. If the user modifies the detected stent-struts in the frame(s) that is located within 250, the CPU 70 determines which stent the modified frame(s) belongs to. In one example, the CPU 70 can show a GUI and request the user to select the stent for each frame that is modified. In another example, the CPU 70 may select a stent based on pre-defined criteria and request that the user through the GUI determine whether the selected stent is acceptable or not. The pre-defined criteria may include a distance from the modified frame(s) to the closest edges of the detected stent regions. Alternatively, the CPU 70 may automatically select a stent based on the pre-defined criteria and notify the user which stent is selected via the GUI. In another example, when the user selects a frame to identify additional stent-struts, CPU 70 can ask the user via the GUI which stent the frame that the user selects should belong to. After modifying the frame(s) and selecting a stent that the modified frame(s) belongs to, the CPU 70 performs the same process that is described above with respect to a single stent implantation.

Referring now to FIG. 24, a case where two stents are implanted with partial overlap is shown. If a user modifies the detected stent-struts in the frame(s) that is located at the outside of the detected stented regions (i.e., within 252 or 253), the CPU 70 performs the same process that is described above. If a user modifies the detected stent-struts in the frame(s) that is located within the overlapped region 254 and if a user added stent-struts in the inner area of the detected stent-struts, CPU 70 re-evaluates stent expansion and stent apposition using the newly added inner stent-struts. If a user modifies the detected stent-struts in the frame(s) in the overlapped region 254 and if the modification is removing the detected stent-struts that are used for stent expansion and stent apposition evaluation, CPU 70 re-evaluates stent expansion and stent apposition after the manual modification. If a user modifies the detected stent-struts in the frame(s) in the overlapped region 254 but if the modification is neither adding a new stent-strut(s) in the inner area nor removing the detected stent-strut(s) that is used for the evaluation, CPU 70 does not re-evaluate stent expansion or stent apposition. If a user modifies the detected stent-struts in the frame(s) that is located within region 255 or region 256, the CPU 70 first identifies whether the modified frame(s) is close to the overlapped region 254. This identification can be done by setting a pre-determined threshold for the distance from the edge of the overlapped region or by manual determination by a user. If the modified frame(s) is identified as the frame(s) in the overlapped region 254, CPU 70 determines which stent the added stent-strut(s) belong to. Then, the CPU 70 re-evaluates stent expansion and stent apposition.

Figure 25:
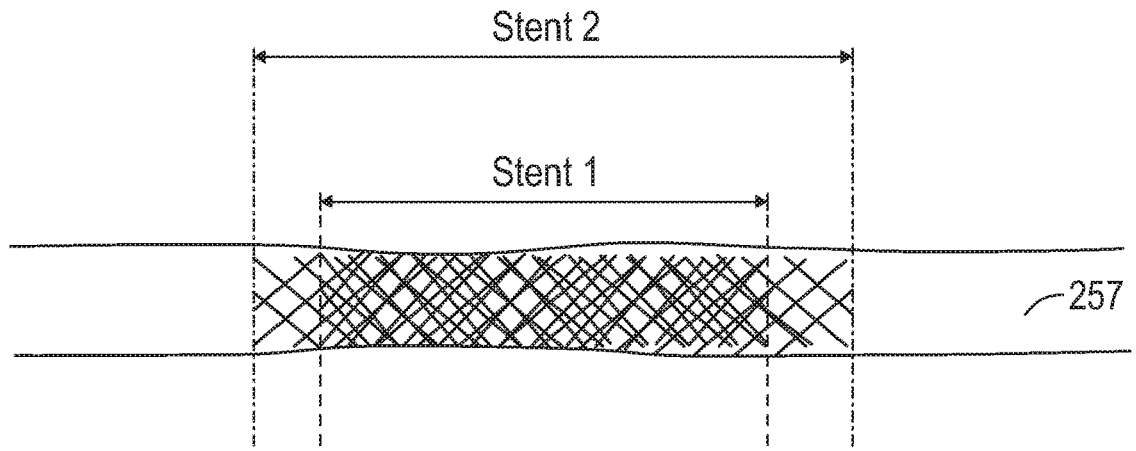
FIG. 25 is a diagram illustrating implantation of two stents with total overlap and examples of the detected result by OCT.
Figure 25:
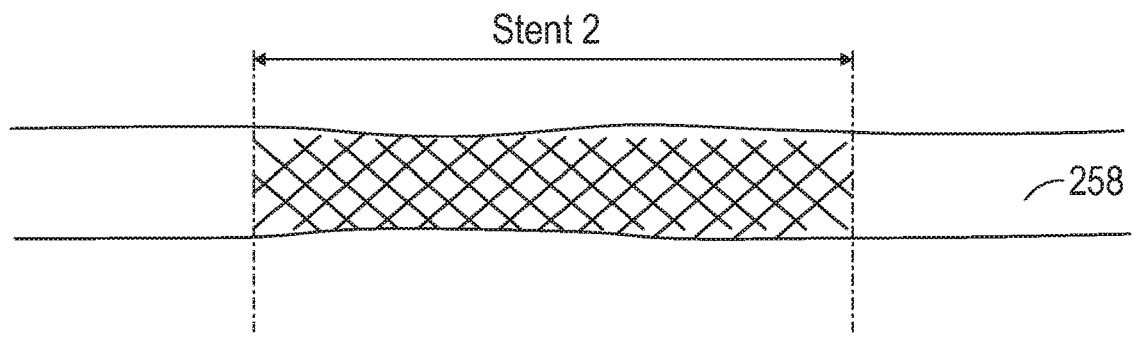
Figure 25:
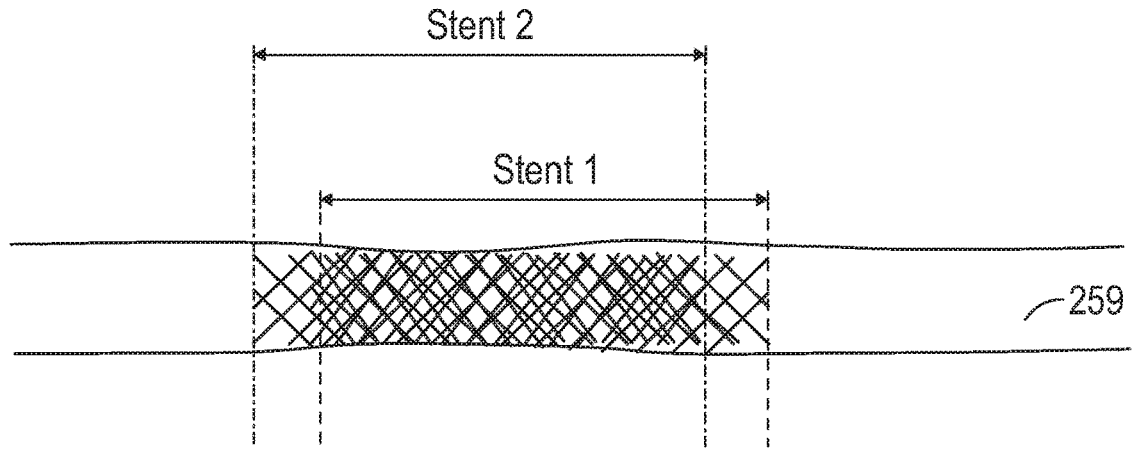

Referring now to FIG. 25, a case where two stents are implanted with total overlap is shown. This may occur when a patient needs in-stent restenosis treated. The vessel 257 illustrates how two stents are implanted with total overlap. In this scenario, it is assumed that Stent 2 is implanted to treat in-stent restenosis for Stent 1. Therefore, Stent 2 should be located in the inner area compared to Stent 1. If CPU 70 detects only Stent 2 (Detected result A, the vessel 258 in FIG. 25), and if a user modifies the detected stent-strut(s), CPU 70 performs the same process as the scenario where only one stent is implanted in the vessel. If CPU 70 detects both stents but not the entirety of at least one stent (Detected result B, the vessel 259 in FIG. 25), and if a user modifies the detected stent-strut(s), CPU 70 performs the same process as described in the above scenario with implantation of two stents with partial overlap.

Figure 26:
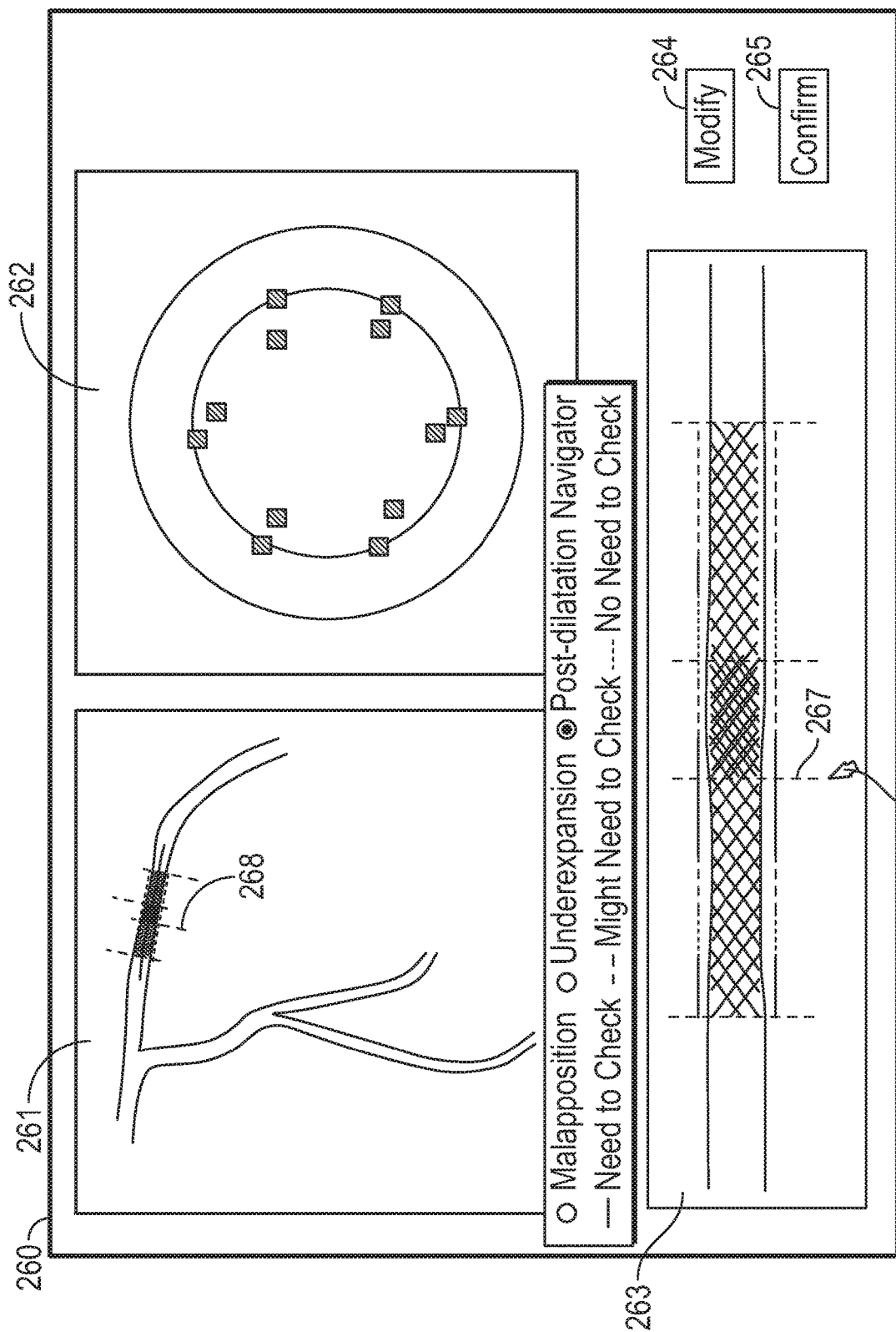
FIG. 26 is an exemplary diagram illustrating a graphical user interface for modifying detection results in accordance with one or more aspects of the present disclosure.

Next in FIG. 26, an example GUI 260 to modify the detection result is illustrated. In this example GUI, it is assumed that co-registration between an angiography image and intravascular image is already performed with any currently available method. The GUI 260 consists of the angiography image 261, the cross-sectional view of the intravascular image 262, and the longitudinal view of the intravascular image 263. In one example, the user may start the modification process by selecting "MODIFY" button 264. Alternatively, the user may start the modification process by selecting anywhere in the angiography image 261, the cross-sectional view of the intravascular image 262, or the longitudinal view of the intravascular image 263. Once the user initiates the modification process, CPU 70 enters a mode to accept any user inputs that result in modifying the detected result. In this example GUI, a user is preparing to modify the detected stent edge 267 in the longitudinal view 263. The CPU 70 then displays an arrow 266 near the detected stent edge 267. To modify the location, the user may select the detected result that the user would like to modify and make a second selection corresponding to the desired location. The user may also drag the detected result to the desired location. Since the angiography image 261 and the intravascular image 262 are co-registered, once the detected stent edge 267 is moved to the desired location, the CPU 70 moves the corresponding stent edge location 268 in the displayed angiography image 261 to the location that the user modified to. If a user modifies the detected result of the stent edge on the angiography image 261, CPU 70 changes the corresponding stent edge in the longitudinal view 263 or in the angiography image 261, CPU 70 displays the corresponding cross-sectional intravascular image frame in 262, so that a user may check whether any stent-struts can be observed at the modified location using the cross-sectional view 262. If the user modifies the detected result in the angiography image 261 or in the longitudinal view 263, once a user selects the location to be modified, the CPU 70 starts the re-evaluation process. If the user prefers, the CPU 70 may start the re-evaluation process after the user selects "CONFIRM" button 265. The "CONFIRM" button 265 is enabled once the user finishes at least one modification.

If the user prefers to modify the detected result in the cross-sectional view 262, the user may initiate the modification process by selecting the "MODIFY" button 264 or by clicking on the displayed detected result in the cross-sectional view 262 by way of example. Then, the user may modify the detected result by selecting the detected result and then selecting a desired location or dragging the detected result to the desired location. If the user would like to remove the detected result or add to the detected result, the user may double-click the detected result or at the location where the user would like to add. Once the user finishes all modifications, the user may let the CPU 70 know that the modification is finished by selecting the "CONFIRM" button 265. After that the CPU 70 starts the re-evaluation process.

Any methods and/or data of the present disclosure, such as the methods for evaluating stent expansion and stent apposition, may be stored on a computer-readable storage medium. A computer-readable and/or writable storage medium used commonly, such as, but not limited to, one or more of a hard disk (e.g., a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM"), a DRAM, a read only memory ("ROM"), a storage of distributed computing systems, a memory card, or the like (e.g., other semiconductor memory, such as, but not limited to, a non-volatile memory card, a solid state drive, SRAM, etc.), an optional combination thereof, a server/database, etc. may be used to cause a processor to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

The above described devices, systems, and methods can be implemented by supplying one or more computer-readable media having stored therein computer-executable instructions for realizing the above described operations to one or more computer devices that are configured to read the computer-executable instructions and execute them. In this case, the system or devices perform the operations of the above-described embodiments when executing the computer-executable instructions. Also, an operating system on the one or more systems or devices may implement the operations of the above described embodiments. Thus, the computer-executable instructions or the one or more computer-readable media storing the computer-executable instructions or the one or more computer-readable media storing the computer-executable instructions thereon constitute an embodiment.

While the above disclosure describes certain illustrative embodiments, the present disclosure is not limited to the above-described embodiments, and the following claims include various modifications and equivalent arrangements within their scope.

What is claimed is:

1. A method for processing an intravascular image including a plurality of image frames acquired during a pullback of an imaging catheter inserted into a vessel, the method comprising:
    displaying on a graphical user interface (GUI) an image including detected results of lumen borders and at least one stent, the image including an evaluated stent expansion and/or an evaluated stent apposition determined from the intravascular image including the plurality of image frames acquired during the pullback of the imaging catheter inserted into the vessel, and the at least one stent having an evaluated stent length;
    determining whether a modification to the displayed detected results of the at least one stent has been received by the GUI;
    re-evaluating stent length, stent expansion, and stent apposition in a case where it is determined that the displayed detected results of the at least one stent have been modified via, and using, the GUI; and displaying the re-evaluated stent expansion and the re-evaluated stent apposition on the GUI after the modification has been received via, and using, the GUI.

2. The method of claim 1, wherein in a case where it is determined that the displayed detected results of the at least one stent have not been modified and a lumen border has been modified via the GUI, then stent expansion and stent apposition are re-evaluated and displayed on the GUI in a case where a position of the modified lumen border including at least one frame from the plurality of image frames is located within a stented region of the vessel defined by the detected results of the at least one stent.

3. The method of claim 2, wherein in a case where it is determined that the position is not located within the stented region and the position corresponds to a reference frame, then stent expansion is re-evaluated and displayed on the GUI.

4. The method of claim 1, wherein in a case where it is determined that a user has modified a stent edge to a position outside an area within a stented region of the vessel defined by the detected results of the at least one stent, at least one new reference frame is selected for re-evaluating the stent length, the stent expansion, and the stent apposition.

5. The method of claim 4, wherein in a case where a calculated stent length is equal to or within a predetermined threshold to an actual stent length, an intravascular image frame at a position representing a distal end of a stented segment and an intravascular image frame at a position representing a proximal end of the stented segment are selected as new reference frames.

6. The method of claim 4, wherein in a case where a calculated stent length is not equal to or within a predetermined threshold to an actual stent length, the at least one new reference frame is selected based on the calculated stent length or the actual stent length.

7. The method of claim 1, wherein it is determined that a user has modified a stent edge to a position located within an area between a first stent edge and a second stent edge of a stented region of the vessel defined by the detected results, the user may select at least one new reference frame or use an original reference frame for re-evaluating the stent length, the stent expansion, and the stent apposition.

8. The method of claim 1, wherein the detected results include a first stented region and a second stented region that does not overlap any portion of the first stented region.

9. The method of claim 8, wherein in a case where it is determined that a user has modified a stent edge to a position outside an area within the first stented region and the second stented region, at least one new reference frame is selected for re-evaluating the stent length, the stent expansion, and the stent apposition.

10. The method of claim 8, wherein in a case where it is determined that a user has modified a stent edge to a position within the first stented region or the second stented region, at least one new reference frame or an original reference frame is used for re-evaluating the stent length, the stent expansion, and the stent apposition.

11. The method of claim 8, further comprising, in a case where it is determined that a user has modified a stent edge to a position located between the first stented region and the second stented region and not within either the first stented region and the second stented region, further determining which stented region the position is associated with based on a pre-defined criteria.

12. The method of claim 11, wherein the pre-defined criteria is a distance from the position to a closest edge of both the first stented region and the second stented region.

13. The method of claim 1, wherein the detected results include a first stented region and a second stented region that partially overlaps with a portion of the first stented region.

14. The method according to claim 13, wherein in a case where it is determined that a user has modified a stent edge to a position located within an overlapped portion of the first stented region and the second stented region, stent expansion and stent apposition are re-evaluated in a case where the user added the second stented region so that the first stented region is closest to the lumen borders.

15. The method according to claim 13, wherein in a case where it is determined that a user has modified a stent edge to a position located within an overlapped portion of the first stented region and the second stented region, stent expansion and stent apposition are re-evaluated in a case where the user removes the first stented region that was previously used for evaluating stent expansion and stent apposition.

16. The method according to claim 1, wherein the detected results include a first stented region and a second stented region with complete overlap of the first stented region.

17. The method according to claim 16, wherein, in a case where the second stented region is located in an inner area with respect to the first stented region and only the second stented region is detected, at least one new reference frame is selected for re-evaluating the stent length, the stent expansion, and the stent apposition in a case where a user has modified a stent edge to a position outside an area of the second stented region, and
in a case where it is determined that the user has modified the stent edge to a position located within an area associated with or of the second stented region, at least one new reference frame or an original reference frame is selected by the user and is used for re-evaluating the stent length, the stent expansion, and the stent apposition.

18. The method according to claim 1, further comprising:
detecting a location of lumen borders and locations of stent struts, from the intravascular image, to obtain the detected results of the lumen borders and the at least one stent.

19. An information processing apparatus for processing an intravascular image including a plurality of image frames acquired during a pullback of an imaging catheter inserted into a vessel, the apparatus comprising:
a memory; and
a processor in communication with the memory, the processor operating to:
display on a graphical user interface (GUI) an image including detected results of lumen borders and at least one stent, the image including an evaluated stent expansion and/or an evaluated stent apposition determined from the intravascular image including the plurality of image frames acquired during the pullback of the imaging catheter inserted into the vessel, and the at least one stent having an evaluated stent length;
determine whether a modification to the displayed detected results of the at least one stent has been received by the GUI;
re-evaluate stent length, stent expansion, and stent apposition in a case where it is determined that the displayed detected results of the at least one stent have been modified via, and using, the GUI; and display the re-evaluated stent expansion and the re-evaluated stent apposition on the GUI after the modification has been received via, and using, the GUI.

20. A non-transitory computer-readable storage medium storing a computer-readable program for causing a computer to execute a method for processing an intravascular image including a plurality of image frames acquired during a pullback of an imaging catheter inserted into a vessel, the method comprising:

displaying on a graphical user interface (GUI) an image including detected results of lumen borders and at least one stent, the image including an evaluated stent expansion and/or an evaluated stent apposition determined from the intravascular image including the plurality of image frames acquired during the pullback of the imaging catheter inserted into the vessel, and the at least one stent having an evaluated stent length;

determining whether a modification to the displayed detected results of the at least one stent has been received by the GUI;

re-evaluating stent length, stent expansion, and stent apposition in a case where it is determined that the displayed detected results of the at least one stent have been modified via, and using, the GUI; and displaying the re-evaluated stent expansion and the re-evaluated stent apposition on the GUI after the modification has been received via, and using, the GUI.

* * * * *